(12) United States Patent
Lyapko

(10) Patent No.: US 10,610,731 B2
(45) Date of Patent: Apr. 7, 2020

(54) BREATHING APPARATUS WITH MEANS FOR REGULATING THE INHALATION AND EXHALATION RESISTANCES

(71) Applicant: Mykola Lyapko, Kiev (UA)

(72) Inventor: Mykola Lyapko, Kiev (UA)

( * ) Notice: Subject to any disclaimer, the term of this patent is extended or adjusted under 35 U.S.C. 154(b) by 764 days.

(21) Appl. No.: 15/308,838

(22) PCT Filed: Jan. 16, 2015

(86) PCT No.: PCT/UA2015/000005
§ 371 (c)(1),
(2) Date: Nov. 3, 2016

(87) PCT Pub. No.: WO2015/171097
PCT Pub. Date: Nov. 12, 2015

(65) Prior Publication Data
US 2017/0157461 A1   Jun. 8, 2017

(30) Foreign Application Priority Data

May 6, 2014   (UA) .............................. a 2014 04852

(51) Int. Cl.
*A63B 23/18*   (2006.01)
*A61M 16/00*   (2006.01)
(Continued)

(52) U.S. Cl.
CPC ......... *A63B 23/18* (2013.01); *A61M 16/0045* (2013.01); *A61M 16/0084* (2014.02);
(Continued)

(58) Field of Classification Search
CPC .......... A61M 16/0045; A61M 16/0084; A61M 16/0866; A63B 23/18; A63B 21/0088
See application file for complete search history.

(56) References Cited

U.S. PATENT DOCUMENTS 3,097,642 A * 7/1963 Russell ................. A61M 16/06
128/205.17
3,710,780 A * 1/1973 Milch .................... A63B 23/18
601/41

(Continued)

*Primary Examiner* — Kathryn E Ditmer
(74) *Attorney, Agent, or Firm* — Irving M. Weiner; Pamela S. Burt; Weiner & Burt, P.C.

(57) ABSTRACT

The invention relates to medical technology, to non-medicinal means for improving physical health and enhancing physical capabilities by means of a breathing system, and specifically relates to devices which are intended for inhaling hypoxic/hypercapnic mixtures having various compositions, and which have an adjustable resistance to inhalation/exhalation. According to a first variant, a breathing exerciser contains a first chamber, which is connected to means for connecting the exerciser to a user's respiratory tract; a second chamber, communicating with the first chamber; a third chamber, communicating with the second chamber; means for adjusting the composition of a breathing mixture; and means for adjusting the resistance to inhalation/exhalation, installed in a channel through which the first chamber and the second chamber communicate. The second chamber communicates with the atmosphere; the third chamber is elastic; means for regulating the composition of a breathing mixture are in the form of adjustable throttling devices installed in the channels through which the second chamber communicates with the third chamber and with the atmosphere; the means for adjusting the resistance to inhalation/exhalation are capable of separately and independently adjusting resistance to inhalation and resistance to exhalation. A second variant is characterized in that a first chamber communicates with a second chamber by means of two parallel channels, in that means for adjusting the resistance to inhalation/exhalation are installed in the parallel channels, and in that a breathing mixture is capable of passing through said channels in mutually opposite directions.

32 Claims, 12 Drawing Sheets

(51) Int. Cl.
*A61M 16/08* (2006.01)
*A63B 21/008* (2006.01)

(52) U.S. Cl.
CPC ...... *A61M 16/024* (2017.08); *A61M 16/0866* (2014.02); *A63B 21/0088* (2013.01)

(56) References Cited

U.S. PATENT DOCUMENTS

| | | | | |
|---|---|---|---|---|
| 4,226,233 | A * | 10/1980 | Kritzer | A63B 23/18 128/204.18 |
| 4,533,137 | A * | 8/1985 | Sonne | A63B 23/18 128/207.16 |
| 4,739,987 | A * | 4/1988 | Nicholson | A63B 23/18 128/207.16 |
| 6,631,716 | B1 * | 10/2003 | Robinson | A61M 16/20 128/204.21 |
| 6,726,598 | B1 * | 4/2004 | Jarvis | A63B 23/18 128/200.24 |
| 2006/0130839 | A1 * | 6/2006 | Bassovitch | A61M 16/0045 128/205.28 |
| 2009/0173348 | A1 * | 7/2009 | Fisher | A61B 5/083 128/205.12 |
| 2010/0163046 | A1 * | 7/2010 | Fisher | A61M 16/00 128/204.18 |
| 2011/0212811 | A1 * | 9/2011 | Rutten | A63B 21/00069 482/13 |
| 2012/0240935 | A1 * | 9/2012 | Johansen | A61M 16/0045 128/205.17 |

* cited by examiner

Unit 1

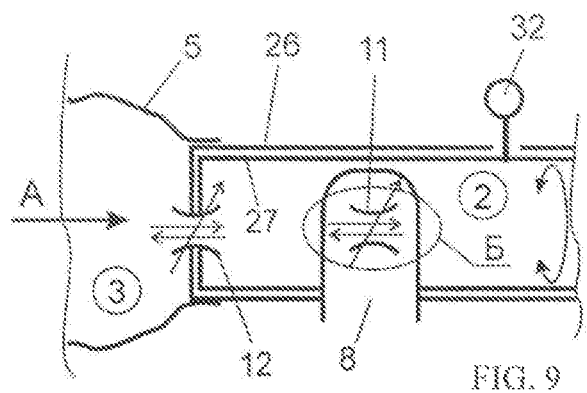
FIG. 9
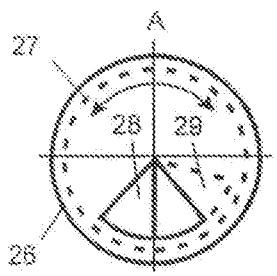 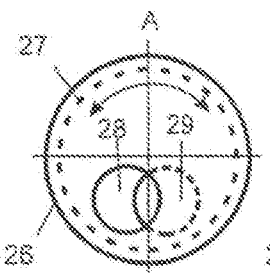 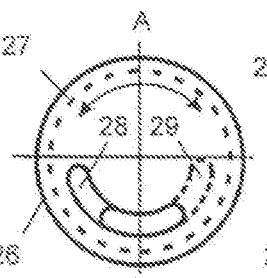 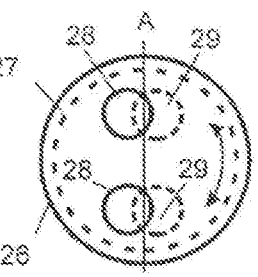
FIG. 10  FIG. 11  FIG. 12  FIG. 13
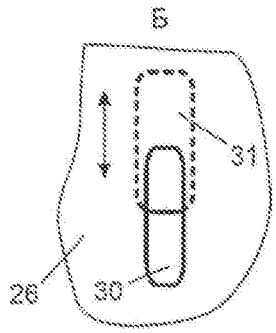 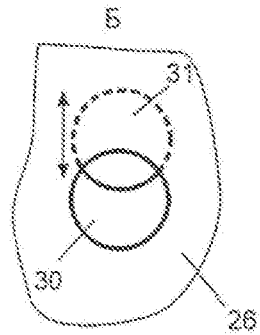 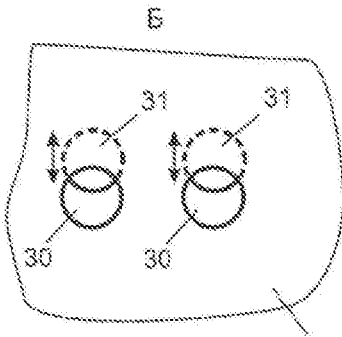
FIG. 14  FIG. 15  FIG. 16
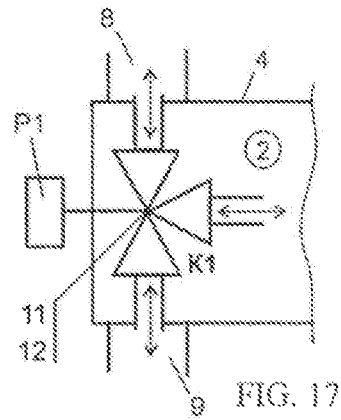 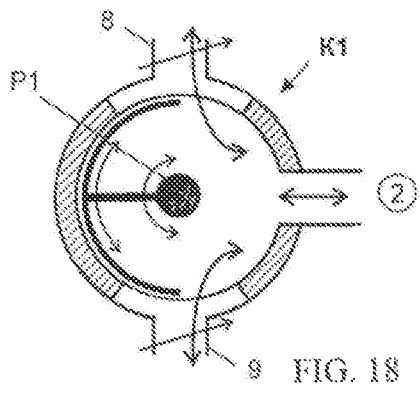
FIG. 17  FIG. 18

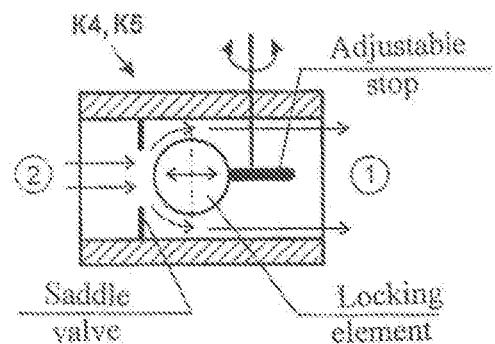
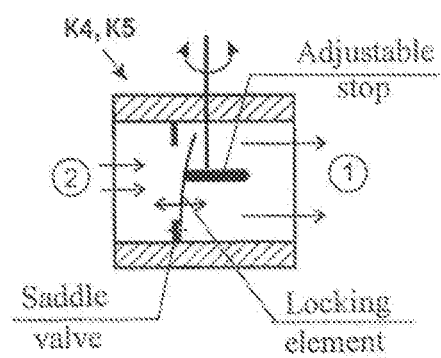
FIG. 24   FIG. 25
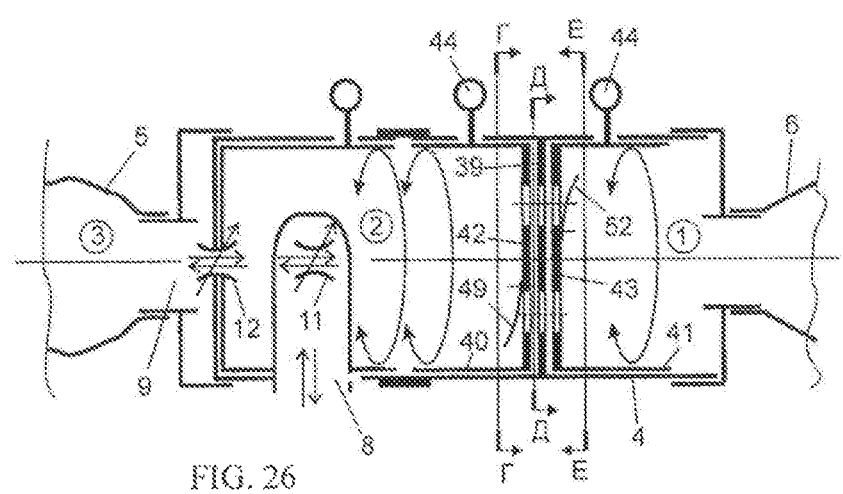
FIG. 26
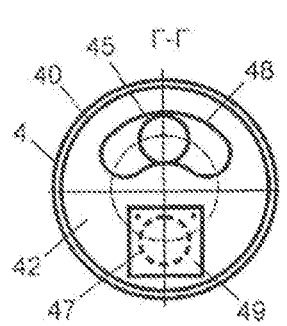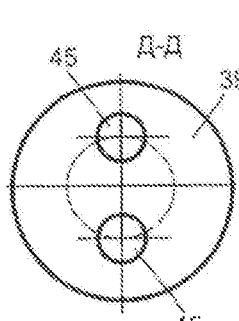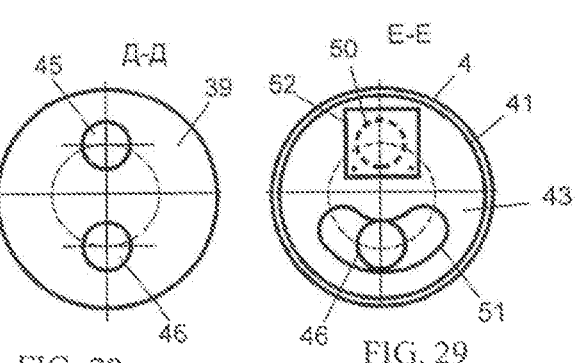
FIG. 27   FIG. 28   FIG. 29

BREATHING APPARATUS WITH MEANS FOR REGULATING THE INHALATION AND EXHALATION RESISTANCES

FIELD OF TECHNOLOGY

The invention relates to medical devices, to non-medicated means of the general therapeutic effects on the body and enhance human physical abilities through the respiratory system, in particular, to adjustable inhalation/exhalation resistance devices for breathing hypoxic-hypercapnic mixtures of different compositions, and can be used in health care purposes in hospitals and in the domestic environment.

BACKGROUND

It is well known that normal (healthy person) own body supports desired levels of carbon dioxide in the blood within 6.5-7.0% (normocapnia). Due to improper breathing and other behavioral factors at stress, physical inactivity, exposure to other adverse factors, as well as with age the deviations from the normal concentration of carbon dioxide in the blood of the human body (deficiency of carbon dioxide or hypocapnia) may occur. As a result, the smooth muscle tone regulation, blood flow to organs are violated, blood pressure is increased, respectively, the severity of hypertension, coronary heart disease, angina, asthma, chronic bronchitis, diabetes, diseases of the digestive tract and other diseases are formed and increased.

For the prevention and treatment of these abnormalities the hypoxic-hypercapnic respiratory training (hypoxic-hypercapnic effect on the body) as well as training with increased inhalation/exhalation resistance (barrier) are widely used.

Hypoxic training is breathing hypoxic mixtures (with a reduced content of oxygen in the mixture). When breathing air mixture with reduced oxygen content the complex of the adaptive reactions develops due to the process of adaptation to hypoxia in the human body which results to the appearance of endogenous type respiration using endogenous oxygen presenting in adipose tissue, and to the combustion of not oxidized products of metabolism in the body into $CO_2$ and $H_2O$ (carbon dioxide and water). As a result of hypoxic breathing the physiological reserves of the body is increased i.e. the reserved capillaries are open, more red blood cells are released into the bloodstream, blood volume increases, blood circulation and oxygen delivery into cells improves, including endogenous oxygen, metabolism normalizes, functional status, performance, vitality of the body and quality of human life improve.

Hypercapnic training is breathing hypercapnic mixtures (with a high content of carbon dioxide in the inhaled air). It is known that carbon dioxide is the most important factor influencing on the most important biological and physiological processes. Carbon dioxide affects on the metabolism of the cells, on the state of the smooth muscles of internal organs and blood vessels, on the condition of the nervous system, on the acid-base balance in the body, on the process of separating oxygen from hemoglobin during the passage of the blood through the capillaries and following entering the tissue. The human body actively reacts to the increasing of the carbon dioxide in the blood and tissues as a result of excitation of hypercapnic chemoreceptors, when reducing the carbon dioxide content such a reaction is not observed, since there are no chemoreceptors in human body, which are responsive to reduction of carbon dioxide. This fact underscores the importance of hypercapnic training for maintaining the required amount of carbon dioxide in the blood and tissues.

Training with increased inhalation/exhalation resistance (barrier) promotes not only improving of the gas exchange, but also increasing of the strength and endurance of the respiratory muscles, and using the entire respiratory system for the recovery of the respiratory system and the whole organism. When increasing the inhalation resistance the inspiratory muscles (mainly the muscles of the diaphragm) are exposed to training. When increasing the exhalation resistance the expiratory muscles (mainly abdominal muscles and intercostal muscles) are exposed to training. Such training besides a positive effect on said respiratory muscles also promotes the bronchi gymnastics, improves lymph drainage and venous outflow, gas exchange at the alveolar level, drainage functions of the bronchial tree, the cleaning process of the bronchi and lungs. Training with the increased inhalation/exhalation resistance (barrier) is mandatory for the athletes, professionals who use respiratory protective equipment i.e. masks, aqualungs, diving suits, and so on.

It is widely known breathing exercises, such as gymnastics of Strelnikova and Buteyko, gymnastics combat systems, which use artificial methods of increasing the inhalation/exhalation resistance in the natural respiratory tract (pressing on nose wings when inspiriting that is increasing inhalation resistance, expiration through clenched teeth with sound "tssss" that is increasing exhalation resistance).

The drawback of the breathing exercises is that carbonation is not controlled by anything other than the own feelings of man, and this is very subjective and can not only improve, but worsen health.

For training of the respiratory system the special devices are used (breathing exercise equipment or breathing exercisers). These devices promote adjusting the inhalation/exhalation resistance, setting up modes of the hypoxic-hypercapnic effects on the body and management of them independently of the subjective feelings of man.

Such devices (breathing exercisers) are widely described in the sources of scientific, technical and patent information. As the analogues of claimed exerciser the following known devices are selected.

Breathing apparatus for carrying out breathing hypoxic stimulation (is known by the USSR inventors certificate number 1526699, IPC A61M 16/00, filing date 15 Mar. 1988).

Breathing apparatus comprises a mask with exhalation/inhalation valves, cartridge absorbing oxygen dioxide, particulate filter, tee, made with internal and external diaphragms and a socket for connecting of the breathing bag with said apparatus, the inhalation/exhalation air channels. Said Inner diaphragm connects inhalation channel with breathing bag and said outer diaphragm connects the same channel with the atmosphere. In diaphragms the passageways are formed.

Breathing apparatus operates as follows.

When expirating the air with reduced oxygen content through the valve and exhalation channel enters the cartridge with a chemical absorber of carbon dioxide and then through the particulate filter flows into the breathing bag and partly discharged into the surrounding atmosphere through the diaphragms.

When inspirating gas mixture with reduced oxygen content from the breathing bag through the opening in the inner diaphragm, through the inhalation channel and the inhalation valve is fed to the inhalating. Simultaneously the inhalation air comes in from the environment through the opening in the outer diaphragm.

Ratio of flows entering the inhalation from the breathing bag and from the surrounding atmosphere is determined by the areas of the openings formed in the inner and outer diaphragms.

Since the amount of air drawn from surrounding atmosphere is determined by the areas of openings formed in the inner and outer diaphragms, the concentration of oxygen in the inhalation gas mixture is set constant.

Common features of the selected analogue and claimed solution are breathing exerciser comprising means of connecting to the airways of user, flexible chamber carried out in the form of breathing bag, channels supplying atmospheric air and gas mixture to the breathing organs from the breathing bag and throttle devices installed in the channels.

Breathing apparatus does not provide regulation of composition of hypoxic-hypercapnic breathing mixture because throttle devices (openings in the diaphragms) are unregulated. The device has no means of creating inhalation/exhalation resistance and regulation of it. All said limits the modes of use of the exerciser and its potential health effects on the body.

It is known the device for the treatment of respiratory and blood circulation (inventor's number 1,607,817 of the USSR, the IPC A61M 16/00, filing date 11 Feb. 1987).

The apparatus comprises the breathing mask, the single inhalation/exhalation channel carried out in form of the sleeve, breathing bag connected to the sleeve, the stabilizer of the inhalation air mixture composition, said stabilizer is carried out in form of a rectangular opening cut in the sleeve, and manual valve mounted on the sleeve with the possibility of longitudinal displacement along said opening and partial overlap of it. Said manual valve is provided with a scale of the oxygen and carbon dioxide content in the inhaled air mixture.

The device operates as follows.

Preliminary the desired content of fresh air in the inhaled air mixture is set according to the scale of said manual valve. Then the breathing mask is fixed on the patient's head.

When exhaling the exhaled air enters mainly the breathing bag through the sleeve, smaller part of it comes out to the atmosphere through the rectangular opening in the sleeve.

When inhaling the exhaled air from the breathing bag enters the sleeve and the atmosphere air through the opening in the sleeve alsow enters sad sleeve, said opening is partial overlapped with manual valve. The both flows are mixed in the sleeve. In a few minutes the inhalation mixture composition (the content of the oxygen and carbon dioxide in the mixture) stabilizes according to the limit instructions of the manual valve scale.

Common features of the selected analogue and the claimed solution are the breathing exerciser comprising means connecting it to the user's airways, the flexible chamber carried out in form of breathing bag, the channels supplying the inhaled atmospheric air and exhaled air from the breathing bag to the human breathing organs, the adjustable valve device installed in the channel for supplying atmospheric air.

Modes of using the exerciser and its potential health effects on the body are limited by the lack of means creating inhalation/exhalation resistance and means regulating said resistance.

It is known the breathing exerciser used as a physiotherapy apparatus (patent number 2,196,612 of the Russian Federation, the IPC A61M 16/00, filing date 7 Jun. 1987).

The exerciser comprises a composite body, means regulating the breathing resistance, the inhalation and exhalation valve devices. Said composite body includes a hollow cylinder and a cup disposed axially in the cavity of said hollow cylinder and connected hermetically by its open end with said hollow cylinder.

In the side wall of the hollow cylinder and in the side wall of said cup the through openings are carried out, said openings are closed on the outside by elastic annular diaphragms. There are located the movable dissected clamps on the hollow cylinder and the cup at the portion of placing of elastic annular diaphragms. Said dissected clamps are mounted to turn them angular relative to the hollow cylinder and the cup and to regulate passage sections of the through openings. At the constant slots in the dissected clamps the regulation of the inhalation/exhalation resistance is ensured by the carrying out of the openings in the form of a series of gradually increasing diameter, or in the form a widening of the slots.

When inhaling the elastic diaphragm mounted on the hollow cylinder and being the exhalation valve closes the openings of the hollow cylinder, and the elastic diaphragm mounted on the cup and being the inhalation valve opens the cup openings located within the slot of the dissected clamp.

When exhaling, the elastic diaphragm being inhalation valve closes the openings of the cup and the elastic diaphragm being the exhalation valve opens hollow cylinder openings within the slot of the dissected clamp.

Common features the selected analogue and claimed solution are the breathing exerciser, including the inhalation and exhalation channels, in which the adjustable throttle devices are installed.

The design of the exerciser does not provide the regulation of the hypoxic/hypercapnic breathing mixture composition, that limits the modes of use the exerciser and its potential health effects on the body.

It is known personal breathing device designed for providing a hypoxic-hypercapnic respiratory mixture (patent number 2,336,907 of the Russian Federation, the IPC A61M 16/00, filing date 2 Jun. 2006).

The device includes a respiratory mask, the inner space of which is connected to two bags for collection of exhaled air through two atmosphere air intakes, which are arranged on both sides of the respiratory mask and provided with the inhaled air mixture regulators. The inhaled air mixture regulators consist of a series of plugs with the through openings of different diameters. The plugs are installed in through openings carried out in the atmosphere air intakes.

The device has separated inhalation and exhalation channels, isolated by the inhalation and exhalation valves, which are disposed in the respiratory mask. The exhalation channels are formed by the exhalation valve and the exhalation tubes connecting the mask interior with the air intakes. The inhalation channels are formed by the atmosphere air intakes provided with the bags attached thereto and the inhalation valves through which the air intakes are connected with the inner space of the mask.

When exhaling (inhalation valves are closed), the air with reduced content of oxygen through the exhalation valve enters the atmosphere air intakes, the bags for collection the exhalation air, and partly discharges into the surrounding atmosphere through the openings in the plugs.

When Inhaling (exhalation valve is closed) inhalation valves opens. Air mixture having the reduced concentration of oxygen and the increased portion of carbon dioxide from the bags for collecting exhaled air through the atmosphere air intakes enters the inhale. Simultaneously, the surrounding atmosphere air enters the inhale through said openings in the plugs. The ratio of flows entering the inhale from the bags and from the surrounding atmosphere through said openings in the plugs is determined by the total aerodynamic resistance of total diameter of the through openings carried out in the plugs and the overall diameter of the inlets in the bags.

Common features of said analog and claimed solution are breathing exerciser, including means connecting said exerciser with the user's breathing airways, the flexible chamber carried out in form of breathing bag, the channels supplying atmosphere air to the human breathing organs and supplying air mixture from the breathing bag, adjustable throttle device installed in the channel supplying the atmosphere air.

Modes of using the exerciser and its potential health effects on the body are limited by the lack of means for providing inhalation/exhalation resistance and its regulation.

It is known breathing exerciser designed for the prevention and treatment of diseases by breathing with hypoxic-hypercapnic air mixture (patent number 2,467,771 of the Russian Federation, the IPC A61M 16/00, filing date 16 Aug. 2010).

Breathing exerciser consists of a mask carried out to connect said exerciser to the user's breathing organs, breathing bag and mixer carried out in the form of regulator of the inhaled air mixture. Said mixer is installed in an opening in the lower part of the mask. The breathing bag is connected to the lower part of said mixer.

Said mixer can be formed as a cylinder in the lower portion of which there is an opening which overlapped by the elastic flexible petals, and on the side surface of which there is an atmospheric air opening also closed by the elastic flexible petals. Elastic flexible petals provide minimal inhalation/exhalation resistance at a constant ratio of fresh air and exhaled air in the breathing mix.

Said mixer can be formed as a cylindrical housing with openings in the lower portion and on the side surface. Inside the housing a cylinder is placed to be rotated manually, the outer diameter of said cylinder is equal to the inner diameter of said housing. Said cylinder is provided with an opening in the cylinder wall and with the base segment. When the cylinder rotates its wall with the opening partially overlaps the opening on a side surface of the housing, and the segment overlaps the part of the opening in the low base of said housing.

At inhalation said mixer regulates the supplying and mixing of two gas flows, i.e. the fresh air from the atmosphere and the mixture from the breathing bag and at exhalation said mixer divides exhaled stream into two flows i.e. the flow enters the breathing bag and the flow enters the atmosphere, providing a predetermined relationship between the fresh air and exhaled air.

Common features of selected analogue and claimed solution are breathing exerciser comprising means to connect to the user's breathing airways, flexible chamber carried out in the form of breathing bag, channels supplying the breathing air and air/gas mixture to the human respiratory organs from the breathing bag.

Modes of using the exerciser and its potential health effects on the body are limited by the lack of means providing the inhalation/exhalation resistance and its regulation.

It is known respirator adapted for preparing hypoxic-hypercapnic respiratory mixture (the inventors certificate of the USSR number 1174043, IPC A62V 18/02, filing date 29 Apr. 1984). Respirator can be used as a exerciser for training and restore breathing users, including athletes.

The respirator consists of a body carried out in the form a hollow rigid cylinder, inside of which the partition is installed to divide the cylinder space into two chambers. The first chamber is connected to the user's respiratory system through the means of communication with the airway respirator (mask with elastic straps). The second chamber is connected to atmosphere via a passage formed in the said body on the portion of the second chamber. The first and second chamber are connected to each other through a channel formed in the partition. The channel of communication the second chamber with the atmosphere is formed in said body in the place most remote from the user's face.

Respiratory is used as follows.

The mask is put on the user's face and fixed on the head with an elastic strap. When breathing during the adoption of procedure, the respiratory gas mixture concentration in the internal volume of the cylindrical body in each cycle of the respirator operation steady mode fluctuates around average values depending on the depth of respiration. If a single chamber of the respirator (without a partition) accommodates the average inhaled mixture composition comprising 18.5% of oxygen and 2.3% of carbon dioxide of total mixture volume, then the series connection of two such cameras gives values of the amount of oxygen and carbon dioxide in the inhaled gas mixture, respectively, 16.5% and 3.7% of the total volume.

Common features of selected analogue and claimed solution are: breathing exerciser comprising two chambers communicating with each other, the first of which is connected to the means for connection said first chamber with the users respiratory tract, and the second chamber is connected with the atmosphere.

Said respirator, when using for hypoxic/hypercapnic training of the human organism, has limited possibilities of regulation of hypoxic/hypercapnic breathing mixture composition, since the variation of the breathing mixtures can be realized only by changing the volume ratio of the first and second chambers, therefore it is required to manufacture several respirators with different volume ratio of said cameras. In said respirator there no means of providing inhalation/exhalation resistance (barrier) and, accordingly, its regulation. All of this limits the use of said respirator and its potential health effects on the body.

It is selected as the prototype the personal breathing exerciser, known for the patent of the Russian Federation RU2118542, IPC A61M 16/00, filing date 30 May 1997.

The personal breathing exerciser contains the inner chamber (the first chamber), connected with the means of the connection said exerciser to the user's breathing airways (breathing tube), the middle (second) chamber connected to the inner (first) chamber, the outer (third) chamber, connected with the middle (second) chamber and the surrounding atmosphere. The inner chamber (the first chamber) is connected with the middle (second) chamber through the openings with means for varying the magnitude flow area of the openings (through an adjustable throttle device). Said exerciser comprises the means for separating a part of the volume the outer (third) chamber (the means of regulating the working volume of the chamber), which are carried out in the form of the transverse partition, adjacent to the inner surface of the outer chamber and the outer surface of the middle chamber, to move axial and to fix said partition, or in the form of at least one inflatable vessel made of elastic material and placed between the outer surface of the middle chamber and the inner surface of the outer chamber.

Therapeutic and preventive effects of said exerciser on the human body is determined by breathing hypoxic-hypercapnic environment and the presence of inhalation/exhalation resistance.

Regulation of hypoxic-hypercapnic respiratory mixture is performed by adjusting of the operating volume of the external (third) camera when setting up exerciser operating mode.

Regulation of the inhalation/exhalation resistance is performed by adjusting the flow cross section of the openings through which the first chamber is connected with the second chamber.

Common features of the prototype and the claimed solution are the breathing exerciser, comprising the first chamber, connected to means connecting said chamber to the user's breathing airways, a second chamber connected to the first chamber, a third chamber connected to the second chamber, means for the regulation of the breathing gas composition and means regulating the inhalation/exhalation resistance.

The design of the breathing exerciser selected as the prototype has the following disadvantages: said design does not allow separately and independently adjust the inhalation resistance and the exhalation resistance; the possibility of the respiratory hypoxic-hypercapnic composition regulation are limited by the size of the third chamber—to provide a high degree of breathing mixture hipercapnia, third chamber should have a significant size; design complexity associated with the need to use the means of change the external (third) chamber working volume.

DISCLOSURE OF INVENTION

The main object of the invention is the improving of the breathing exerciser, in which due to design features it is possible the regulation (change) of hypoxic-hypercapnic respiratory mixture in a wide range by simple technical means, and the separate and independent regulation of the inhalation resistance and exhalation resistance (obstruction, barrier), which extends the possibilities of choice modes of use of the exerciser and its health effects on the body.

In appliance with the first embodiment of the invention said object is achieved in that in the breathing exerciser, comprising the first chamber including means connecting of said exerciser to the exerciser users airways, the second chamber connected to the first chamber, the third chamber connected to the second chamber, means regulating breathing gas composition, means regulating the inhalation/exhalation resistance, said means are installed in the channel of communication the first chamber with the second chamber, according to the invention, the second chamber is connected with the atmosphere, a third chamber is carried out elastic, means regulating the breathing gas composition are carried out in the form of the adjustable throttling device, installed in the channel of communication the second chamber with the third chamber, and the adjustable throttling device is installed in the channel of communication the second chamber with the atmosphere, and means regulating the inhalation/exhalation resistance are carried out to regulate the inhalation resistance and the exhalation resistance separately and independently.

Said features are essential features within the first embodiment of the invention, because they provide hypoxic-hypercapnic respiratory mixture regulation (ratio of oxygen $O_2$ and carbon dioxide $CO_2$ in the breathing mixture) in a wide range with simple technical means, as well as the separate and independent regulation of the inhalation resistance and the exhalation resistance that extends the modes of use of the exerciser and its potential health effects on the user's body.

Means regulating respiratory gas composition and the inhalation resistance and exhalation resistance the exerciser carried out according to the first embodiment can have various circuit implementation.

Means regulating the inhalation resistance and exhalation resistance can be carried out in the form of the adjustable throttling device with a locking element which is installed in the passage section of said throttling device to be moved in opposite directions relative to the plane of the passage section, and an adjustable stops limiting said moving.

The locking element of the adjustable throttling device can be configured in the form of a ball freely established, or in the form of a console petal with the possibility elastic deflection in opposite directions.

These implementations of the locking element are technical equivalents, providing the separate and independent regulation of the inhalation resistance and the exhalation resistance.

Means regulating the inhalation resistance and the exhalation resistance can be carried out in the form of the parallel connected check valve and the adjustable throttling device, as well as in the form of the adjustable throttling device, connected in series with said parallel connected throttling device and said check valve.

The check valve may be arranged in the flow direction towards the first chamber or towards the second chamber.

When the check valve is arranged in the flow direction towards the first chamber the exhalation resistance is always higher than the inhalation resistance. When the check valve is arranged in the flow direction towards the second chamber the inhalation resistance is always higher than the exhalation resistance. This further extends the modes of use of the exerciser.

Adjustable throttling devices installed in the channels of communication the second chamber with the atmosphere and with the third chamber may be carried out in the form of a window cut out in the second chamber housing, and the sleeve hermetically connected with the third chamber and mounted on the second chamber housing to be moved along said window.

Adjustable throttling devices, installed in the channels of communication the second chamber with the atmosphere and with the third chamber, may also be carried out in the form of the sleeve mounted on the second chamber housing to rotate about the longitudinal axis of the housing with the openings cut in the second chamber housing and in the sleeve on the portion located within the third chamber, and with the openings cut in the second chamber housing and in the sleeve on the portion, located outside the third chamber, said openings are arranged to overlap each other and to form when sleeve turning regulated in opposite directions flow sections connecting the second chamber with the third chamber and with the atmosphere.

Such embodiment allows by a working body (moving or rotating the sleeve) at the same time to control the adjustable throttling devices, installed in the channels of communication the second chamber with the atmosphere and with the third chamber, depending on setting (a decrease the degree of throttling in one throttling device with a simultaneous increasing the degree of throttling in the other throttling device) that provides the convenience of using the breathing exerciser and increase the depth of regulation of said throttling devices.

The adjustable throttling devices, installed in the channels of communication the second chamber with the atmosphere and with the third chamber, may be carried out in form of the outer cup and inner cup, said inner cup is placed within said outer cup to rotate around the longitudinal axis and to contact the inner cup bottom with the outer cup bottom, said inner and outer cup bottoms are carried out with the openings which are cut to overlap of each other and to form controlled flow section, communicating the second chamber with the third chamber, said inner and outer cups are carried out with the wall openings, which are cut to overlap of each other and to form controlled flow section, communicating the second chamber with the atmosphere, said bottoms openings of the inner and the outer cups are carried out to change the values of their flow section areas and said wall openings of the inner and the outer cups are carried out to change the values of their flow section areas in opposite directions when turning the inner cup.

Adjustable throttling devices installed in the channels, communicating the second chamber with the atmosphere and with the third chamber, may be carried out in the form of a three-way mixing valve with two adjustable channels to reduce the respiratory mixture resistance in one of the regulated channels and at the same time to increase the respiratory mixture resistance in the other regulated channel, and vice versa, using a single control handle of the three-way mixing valve.

Adjustable throttling devices installed in the channels, communicating the second chamber with the atmosphere and the third chamber and installed in the first channel of communication the first chamber and the second chamber with each other, may be carried out in the form of a three-way mixing valve with three adjustable channels to reduce the respiratory mixture resistance in one of the regulated channels and at the same time to increase the respiratory resistance in the other regulated channel, and vice versa, and as well as to provide the independent regulation of the respiratory mixture resistance in the third channel using a single control handle of the three-way mixing valve.

Such embodiment of the adjustable throttle devices in the form of three-way mixing valves with two or three adjustable channels and with a single control handle provides the ease of use exerciser, simplifies its design while maintaining the wide opportunities of regulatory regimes of using the exerciser.

In appliance with the second embodiment of the invention the object is achieved that in the breathing exerciser, comprising the first chamber connected to means communicating said chamber with the exerciser user's airways, the second chamber connected to the first chamber, the third chamber connected to the second chamber, means for regulating the respiratory mixture composition and means for regulating the inhalation/exhalation resistance according to the invention, the third chamber is carried out elastic, the second chamber is connected to the atmosphere, the first chamber is connected by two parallel channels with the second chamber, the means for regulating the respiratory mixture composition are carried out in the form of an adjustable throttling device installed in the channel of communication the second chamber with the third chamber, and in the form of the controlled throttling device, installed in the channel of communication the second chamber with the atmosphere, and means for regulating the inhalation/exhalation resistance are carried out in the form of series-connected check valves and adjustable throttling devices installed in parallel channels of communication the first chamber with the second chamber to provide the respiratory mixture passing through said channels in mutual opposite directions.

These features are essential features of the invention of the second embodiment, as they provide the possibility of regulation of hypoxic-hypercapnic respiratory mixture (ratio of oxygen $O_2$ and carbon dioxide $CO_2$ in the breathing mix) in a wide range with simple technical means, as well as the possibility of separate and independent regulation of the inhalation resistance and the exhalation resistance, flow separation of inhalation and exhalation with the possibility of separate control parameters of gas-air mixtures of inhalation and exhalation, which extends the modes of use of the exerciser and its potential health effects on the body of the user.

Adjustable throttling devices installed in the channels of communication the second chamber with the atmosphere and with the third chamber may be carried out in the form of a three-way mixing valve with two adjustable channels to reduce the respiratory mixture resistance in one of the regulated channels and at the same time to increase the respiratory mixture resistance in the other regulated channel, and vice versa, using a single control handle. This embodiment provides ease of use exerciser and simplifies its design while maintaining the regulatory regimes opportunities of use the exerciser.

The series-connected check valves and adjustable throttling devices installed in the channels of communication the first chamber with the second chamber may be carried out in the form of non-return valves with the means regulating the degree of the forward direction flow throttling.

Means regulating the degree of the forward direction flow throttling can be carried out in the form of an adjustable stop limiting the amount of the locking member movement towards the non-return check valve opening.

This construction is one of the possible executions of the means regulating the inhalation/exhalation resistance in the exerciser according to the second embodiment of our invention.

The series-connected check valves and adjustable throttling devices installed in channels of communication the first chamber with the second chamber may include a transverse partition fastened in the cylindrical housing, inner cups installed within the cylindrical housing on both sides of the partition to rotate about the longitudinal axis and to contact by the cup bottoms with the partition, the pairs of diametrically opposed openings formed in the partition and the cup bottoms, check valves carried out in the form of petals, overlapping one of the openings in the cups bottoms on the inner cups sides, said cups bottom openings, disposed oppositely to the openings with the non-return check valves, are carried out in the form of circular slots, the non-return check valve opening in the bottom of one of the cup, and the slot in the bottom of the cup are located axially with one of the partition openings.

The first and the second chambers may be carried out in the form of the annular hollow hosing, the cavity of which is divided into communicated with each other the first chamber and the second chamber.

In appliance with the third embodiment of our invention the object is achieved that in the breathing exerciser, comprising the first chamber connected to means connecting said exerciser to the user's airways, the second chamber connected to the first chamber, the third chamber connected to the second chamber, means regulating the respiratory mixture composition and the inhalation/exhalation resistance, according to the invention, the third chamber is flexible, the exerciser comprises a respiratory mixture source, the second chamber is divided into two cavities, the first cavity of the second chamber is connected with the first chamber, with the atmosphere and with the third chamber, the second cavity of the second chamber is connected with the third chamber, with the respiratory mixture source and with the first chamber, and the means regulating the respiratory mixture composition and the inhalation/exhalation resistance are carried out in the form of the series-connected non-turn check valves and adjustable throttling devices installed in the channel of communication the first chamber with the first cavity of the second chamber in the flow directed towards the first cavity of the second chamber, in the channel of communication the first cavity of the second chamber with the atmosphere in the flow directed towards the atmosphere, in the channel of communication the first cavity of the second chamber with the third chamber in the flow directed towards the third chamber, in the channel of communication the third chamber with the second cavity of the second chamber in the flow directed towards the second cavity of the second chamber in the channel of communication the second cavity of the second chamber with the first chamber in the flow directed towards the first chamber, in the channel of communication the second cavity of the second chamber with the respiratory mixture source in the flow directed towards the second cavity of the second chamber.

Said features are essential features of the invention according to the second embodiment of the invention, because they provide the possibility of regulation of hypoxic/hipercapnic respiratory mixture (ratio of oxygen $O_2$ and carbon dioxide $CO_2$ in the breathing mix) in a wide range by the simple technical means, as well as the possibility of separate and independent regulation of the inhalation resistance and the exhalation resistance, flow separation on inhalation and exhalation with the possibility of the parameters separate control of the inhaled gas-air mixtures and exhaled gas-air mixtures, the possibility of using special respiratory mixtures, independently the of the surrounding atmosphere, which extends the modes of use of said exerciser and its potential health effects on the body.

The second cavity of the second chamber may be communicated with the atmosphere as the breathing mixture source.

The respiratory mixture source may be carried out in form of the atmosphere communicated chamber for the respiratory mixture preparation, in the cavity of said chamber the natural or synthetic essential oils and/or the curative herbs and/or the herbal extracts, and/or the mineral substances such as mineral salts, with heating means or without them are located. This embodiment of our invention increases the performance of the health effect when exerciser using as a result of the presence of the therapeutic respiratory mixture additives.

The respiratory mixture preparation chamber may be carried out to receive therein the user's body or the user's body part, such as the user's head. In this embodiment of our invention the breathing mixture therapeutic additives not only health effect on the user's respiratory system, but also on the exposed areas of the user's body, which increases further the healing effect.

The respiratory mixture source may be carried out in form of the irrespective breathing mixture source, such as the throttle device regulated LPG with the breathing bag. Such an embodiment of our invention provides the respiratory mixture using in the exerciser independently on the environmental conditions.

The first and second chambers may be carried out in the form of an annular hollow housing, the cavity of which is divided into the first chamber, the first cavity of the second chamber, and the second cavity of the second chamber communicating between each other. This solution is an example of the possible housings using in the third embodiment of the exerciser.

The adjustable throttling devices installed in the channels of communication the first cavity of the second chamber with the atmosphere and with the third chamber, and also the adjustable throttling devices installed in the channels of communication the second cavity of the second chamber with the third chamber and with the respiratory mixture source may be carried out in the form of the three-way mixing valves provided with two adjustable channels to reduce the respiratory mixture resistance in one of the regulated channels and at the same time to increase the respiratory mixture resistance in the other regulated channel, and vice versa, using single control handles.

The adjustable throttling devices, installed in the channels of communication the first cavity of the second chamber, with the atmosphere, with the third chamber and with the first chamber, and the adjustable throttling devices installed in the channels of communication the second cavity of the second chamber with the third chamber, with the respiratory mixture source and the first chamber, may be carried out in the form of the three-way mixing valve with three adjustable channels to reduce the respiratory mixture resistance in one of the regulated channel while to increase the respiratory mixture resistance in the other regulated channel, and vice versa, as well as to regulate the respiratory mixture resistance in the third channel using the single control handle.

The adjustable throttle devices carried out in the form of three-way mixing valves provided with two or three adjustable channels regulated with a single control handle ensure using exerciser ease, simplify its design while maintaining the regulation regime opportunities when using the exerciser.

The series-connected non-return check valves and adjustable throttling devices, installed in the channel of communication the first chamber with the first cavity of the second chamber, in the channel of communication the first cavity of the second chamber with the atmosphere, in the channel of communication the first cavity of the second chamber with the third chamber, in the channel of communication the third chamber with the second cavity of the second chamber, in the channel of communication the second cavity of the second chamber with the first chamber, in the channel of communication the second cavity of the second chamber with the respiratory mixture source, may be carried out in the form of the non-return check valves provided with means regulating the flow throttling degree in the forward direction. Such a solution is yet another example of the possible implementation of the means regulating the respiratory mixture composition and the inhalation/exhalation resistance according to the third exerciser embodiment.

Each of the adjustable throttling devices installed in the channels of communication the first chamber with the first and second cavities of the second chamber may include the outer cup and placed within it the inner cup, carried out to rotate around the longitudinal axis and to contact by the cup bottoms with each other; and the openings carried out in said cup bottoms to overlap mutually of each other and to form the regulated passage sections for communication the first chamber with the first and second cavities of the second chamber when independent turning the inner cup; each pair of adjustable throttling devices, installed in the channels of communication the first cavity of the second chamber with the atmosphere and the third chamber, and in the channels of communication the second cavity of the second chamber with the third chamber and with the respiratory mixture source, may be carried out in the form of the same two cups, provided with the bottom openings and the wall openings; said openings are carried out to overlap of each other and to form regulated passage sections of communication the first cavity of the second chamber with the atmosphere and with the third chamber, and the second cavity of the second chamber with the third chamber and with the respiratory mixture source, when independent turning inner cup; and said openings are also carried out to change the values of the bottom passage sections and the wall passage sections of the cups in opposite flow directions when turning inner cup.

The respiratory mixture pressure sensor and/or the respiratory mixture composition sensor and/or respiratory mixture flow rate sensor can be installed at least in one of the chambers or channels to represent visually the sensor readings to the exerciser user. This allows the user to control separately the respiratory mixture parameters of the inhalation and the exhalation and to regulate independently the using exerciser mode via controlled throttle devices.

The exerciser can be configured with the computer system controlling operating mode, said computer system includes the respiratory mixture pressure sensors and/or the respiratory mixture composition sensors and/or the respiratory mixture flow rate sensors installed at least in one of the chambers or the channels and is provided with the processor predetermining algorithms of the operating exerciser modes, said processor is carried out to present the readings to the user about the operating exerciser modes; with the input unit connected to said sensors and said processor, and with the output unit connected to the unit controlling said throttle devices and said processor. Said computer control system of the operating exerciser mode allows to select the desired mode from a variety of algorithms when using the exerciser and to maintain the selected mode without user participant.

The first chamber of the exerciser can be provided at least one partition wall, on which at least one voice strap is mounted, with one at least voice tab. This embodiment of our invention provides the generation, in the respiratory mixture near at the user's respiratory airways, acoustic vibrations predetermined frequency, the dynamic impact of which on the user's respiratory system organs increases the healing granting by the proposed exerciser.

Means connecting the exerciser to the users airways may be carried out in form of a tube with a mouthpiece or in form a face hermetic mask or in form a hermetic helmet or in form an airtight suit.

BRIEF DESCRIPTION OF DRAWINGS

Description of claimed breathing exerciser and its operation is represented with references to the drawings showing:

FIG. 9—Breathing exerciser, the first embodiment, the scheme of the implementation throttling devices regulating the respiratory mixture composition in the form of the cups.

FIG. 10—Breathing exerciser, the first embodiment, the view A in FIG. 9, the implementation of sector openings in the cup bottoms.

FIG. 11—Breathing exerciser, the first embodiment, the view A in FIG. 9, the implementation of the circular opening in the cup bottoms.

FIG. 12—Breathing exerciser, the first embodiment, the view A in FIG. 9, carrying out the openings in the form of circular slots in the cup bottoms.

FIG. 13—Breathing exerciser, the first embodiment, the view A in FIG. 9, the implementation of two pairs of circular openings in the bottom cups.

FIG. 14—Breathing exerciser, the first embodiment, the view B in FIG. 9 of the carrying out the rectangular openings in the cup walls.

FIG. 15—Breathing exerciser, the first embodiment, the unit B in FIG. 9, the implementation of the circular openings in the cup walls.

FIG. 16—Breathing exerciser, the first embodiment, the unit B in FIG. 9, the carrying out of two pairs of the circular openings in the form of cup walls.

FIG. 17—Breathing exerciser, the first embodiment, carrying out the throttling devices in the form of the three-way mixing valve with two regulated channels.

FIG. 18—Breathing exerciser, the first embodiment, the scheme of the implementation and operation of three-way mixing valve with two regulated channels.

FIG. 24—Breathing exerciser, the second embodiment, the scheme of the non-return check valve of ball type with means regulating the degree of the flow choking in the forward direction.

FIG. 25—Breathing exerciser, the second embodiment, the scheme of the non-turn check valve with the petal type means regulating the degree of the flow choking in the forward direction.

FIG. 26—Breathing exerciser, the second embodiment, the example of the implementation adjustable throttling devices and non-return check valves.

FIG. 27—Breathing exerciser, the second embodiment, the section on line G-G in FIG. 26.

FIG. 28—Breathing exerciser, the second embodiment, the section on line D-D in FIG. 26

FIG. 29—Breathing exerciser, the second embodiment, the section on line E-E in FIG. 26.

EMBODIMENT OF THE INVENTION

Below are described examples of the embodiment of the claimed breathing exerciser and its operation with reference to the drawings.

Figure 1:
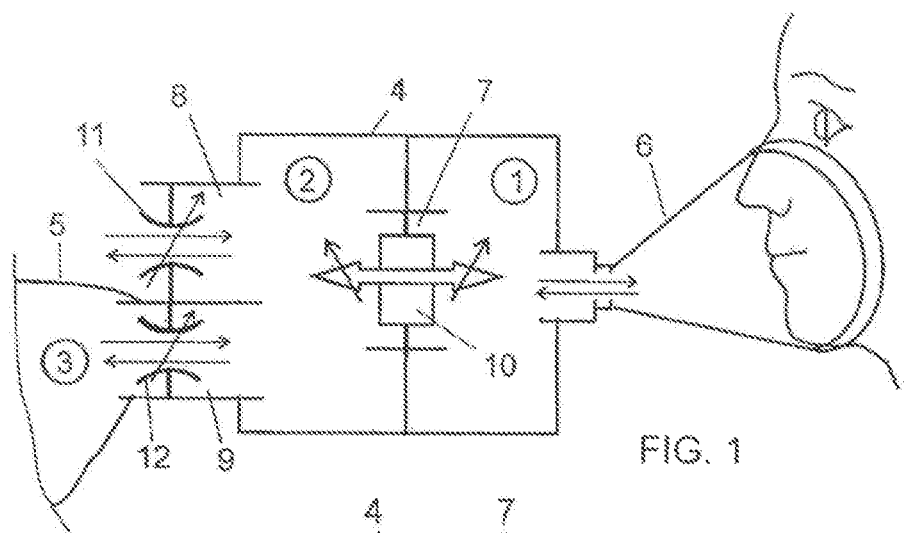
FIG. 1—Breathing exerciser, the first embodiment.

According to the first embodiment (FIG. 1) the breathing exerciser comprises three chambers communicating with each other: the first chamber 1, the second chamber 2, the third chamber 3. The chambers 1, 2 are carried out in the housing 4. The chamber 3 is carried out in the form of an elastic breathing bag 5 connected with the housing 4. The chamber 1 is connected with the connection means 6 to the exerciser user's airways and communicates with the chamber 2 through the channel 7. The chamber 2 is communicated with the atmosphere through the channel 8 and with the chamber 3 through the channel 9.

Means 10 regulating the inhalation/exhalation resistance are installed in the channel 7 of communication with the first chamber 1 and the second chamber 2 carried out to regulate separately and independently the inhalation and exhalation resistance.

Means regulating the respiratory mixture composition are carried in the form of the adjustable throttling device 11 installed in the channel 8 of communication of the second chamber 2 with the atmosphere, and the adjustable throttling device 12 installed in the channel 9 of communication of the second chamber 2 with the third chamber 3.

When exhaling, the carbon dioxide enriched respiratory mixture fills the chamber 1 and then through the channel 7, wherein the means 10 regulating the inhalation/exhalation resistance are installed, enters chamber 2. Part of the exhaled mixture from the chamber 2 is released out into the atmosphere through the channel 8 and installed in it adjustable throttling device 11, the remainder of the exhaled mixture through the passageway 9 enters the chamber 3. The ratio of these parts of said exhaled mixture is set by the flow throttling degree in the channels 8, 9 by means of adjustable throttling devices 11 and 12.

When inhaling, the chamber 2 is supplied with the atmospheric air through the channel 8 and installed in said channel 8 the adjustable throttling device 11, and said chamber 2 is supplied with the respiratory mixture from the elastic chamber 3 through the channel 9 and installed in said channel 9 the adjustable throttling device 12. The amount of the atmospheric air and the respiratory mixture from the chamber 3 entering into the chamber 2 is set by the adjustable throttling devices 11 and 12. Herewith in the chamber 2 the mixing of the atmospheric air with the respiratory mixture from the chamber 3 takes place. The respiratory mixture from the chamber 2 through the channel 7 and, installed in said channel, the means 10 of regulation the inhalation/exhalation resistance enters the chamber 1, wherein is further mixed with the exhaled mixture and then the means 6 of connection the exerciser to the user's respiratory airways. Thus, by mixing in the chambers 1, 2, exhaled respiratory mixture with atmospheric air, the given respiratory mixture composition is supplied to the exerciser user's airways.

Such an execution of exerciser provides the regulation of the inhaled respiratory mixture composition (ratio of oxygen $O_2$ and carbon dioxide $CO_2$), which is defined by adjustable throttling devices 11 and 12, and also provides separate and independent regulation of the inhalation resistance and the exhalation resistance by dint of means 10.

The means 10 regulating inhalation/exhalation resistance installed in the channel 7 of communication the first chamber 1 with the second chamber 2 can be carried in form of the adjustable throttle device with the locking elements (13, 14) installed in the passage section of the device to move in opposite directions concerning to flow section plane, and the adjustable stops 15 limiting the amount of these movements.

Figure 2:
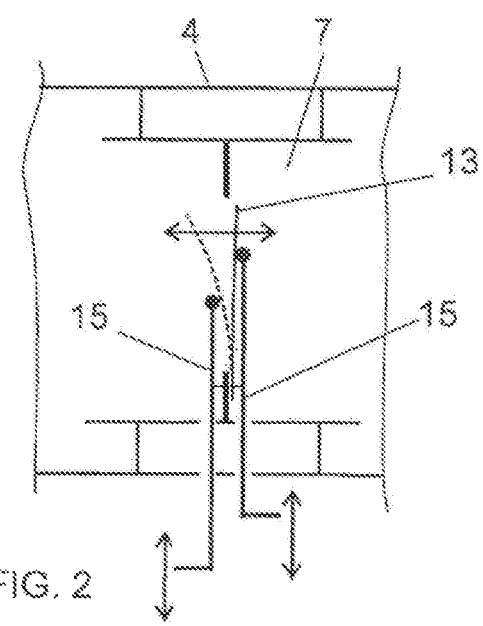
FIG. 2—Breathing exerciser, the first embodiment, the throttling device regulating the inhalation/exhalation resistance with the locking element in the form of the petal.
Figure 3:
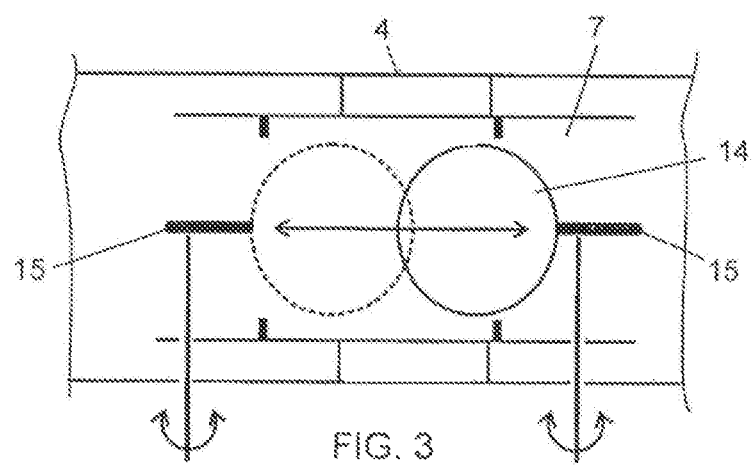
FIG. 3—Breathing exerciser, the first embodiment, the throttling device regulating the inhalation/exhalation resistance with a locking element in the form of the ball.

The locking element of the adjustable throttling device can be carried in the form of the console in form of petal 13 (FIG. 2) to deflect resiliently in the opposite directions or in the form of the freely installed ball 14 (FIG. 3).

Figure 4:
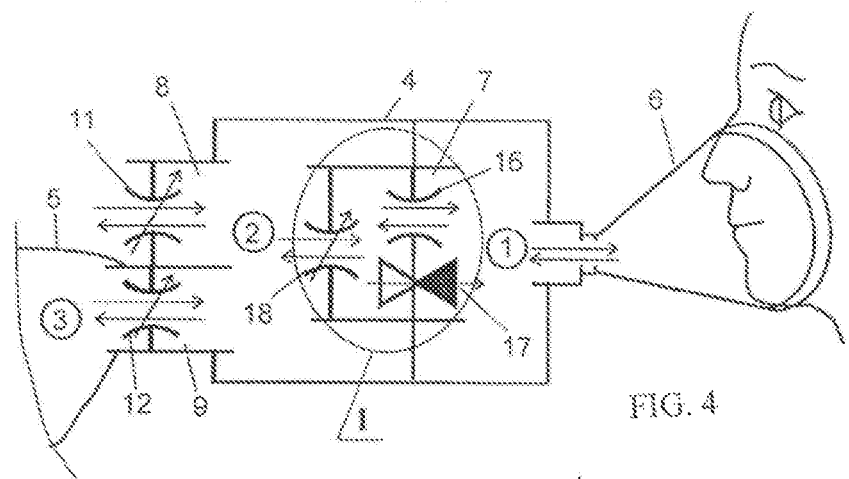
FIG. 4—Breathing exerciser, the first embodiment, the means regulating inhalation/exhalation resistance in form of a throttling device and a non-turn check valve device.

The means regulating the inhalation/exhalation resistance can be carried in the form of the parallel-connected adjustable throttling device 13 and non-return check valve 14 and adjustable throttling device 15 connected in series with said throttling device 13 and check valve 14 installed in the channel 7 of communication the chamber 1 with the chamber 2. The non-return check valve 13 may be carried to direct the respiratory mixture flow in the direction toward the chamber 1 (FIG. 4).

When exhaling the enriched with carbon dioxide respiratory mixture from the chamber 1 through the adjustable throttling device 13 and the adjustable throttling device 15 enters the chamber 2. Herewith the non-return check valve 14 is closed. Part of the exhaled mixture is released from the chamber 2 into the atmosphere through the channel 8 and through the installed in said valve adjustable throttling device 11, the remainder of the exhaled mixture is supplied into the elastic chamber 3 through the channel 9 and through the installed in said channel the adjustable throttling device 12. The ratio of these parts of the exhaled mixture is governed by the degree of the flow choking in the channel 8 by the adjustable throttling device 11, and by the degree of the flow choking in the channel 9 by the adjustable throttling device 12. Herewith the exhalation resistance is regulated by the devices 13, 15.

When inhaling the chamber 2 receives the atmospheric air through the adjustable throttling device 11 and the respiratory mixture of the elastic chamber 3 through the adjustable throttling device 12. The ratio of the atmospheric air and the respiratory mixture of the chamber 3 which enter the chamber 2, is defined by adjustable throttling devices 11 and 12. The respiratory mixture from the chamber 2 through the throttling device 15, through the opened non-turn check valve 14 and partly through the adjustable throttling device 13 flows into the chamber 1 and further to the means 6 of connection the exerciser to the user's airways. Herewith the inhalation resistance is regulated by the throttling device 15.

The blending of the exhaled mixture with the atmospheric air and the regulation of the respiratory composition are similar to that described above.

Such an execution provides the separate regulation of the exhalation resistance which is given by the adjustable throttling devices 13 and/or 15 and the inhalation resistance which is given mainly by said adjustable throttling device 15, and also the regulation of the inhaled mixture composition (ratio of oxygen $O_2$ and carbon dioxide $CO_2$) which is given by the adjustable throttling devices 11 and 12. Herewith the exhalation resistance is always higher than the inhalation resistance because when exhaling the respiratory mixture choking executes through the in series connected adjustable throttle devices 13, 15, and when inhalation the respiratory mixture throttling executes only through the adjustable throttling device 15.

Figure 5:
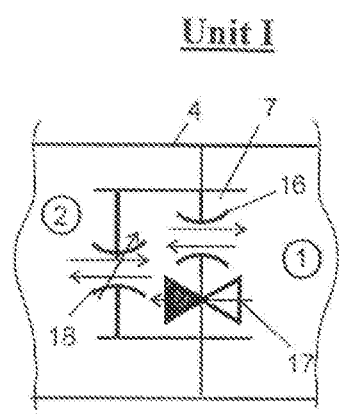
FIG. 5—Breathing exerciser, the first embodiment, the unit I in FIG. 4.

The check valve 14 may be carried to direct the flow towards the chamber 2 (FIG. 5).

When exhaling the enriched with carbon dioxide respiratory mixture from the chamber 1 through the open non-return check valve 13 and the adjustable throttling device 15 enters the chamber 2. Herewith the exhalation resistance is regulated with the throttling device 15. While inhaling the respiratory mixture from the chamber 2 through the adjustable throttling devices 15, and the non-return check valve 13 enters the chamber 1 and then the respiratory mixture enters the means 6 of connection the exerciser to the user's airways. Herewith the non-return check valve 14 is closed.

Herewith the inhalation resistance is always higher than the exhalation resistance as when inhaling the respiratory mixture choking is carried with in series connected adjustable throttling devices 15, 13, and when exhaling the respiratory mixture choking is carried only with the adjustable throttling device 15.

The blending of the respiratory mixture with an atmospheric air and regulating the respiratory mixture composition is similar to those described above.

Such an execution of the exerciser provides the separate regulation of the inhalation resistance which is given by the adjustable throttling device 13 and/or by the adjustable throttling device 15, and the exhalation resistance which is set advantageously by the adjustable throttling device 15, as well as the regulation of the respiratory mixture composition (ratio of oxygen $O_2$ and carbon dioxide $CO_2$) which is set by the adjustable throttling device 11 installed in the channel 8 of communication the chamber 2 with the atmosphere and by the adjustable throttling device 12 installed in the channel 9 of communication the chamber 2 with the chamber 3.

Adjustable throttling devices are widely used in various breathing apparatus and may have a different design, including schemes that are shown in FIG. 2, 3.

Figure 6:
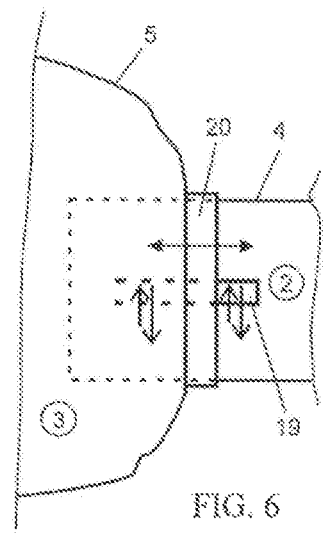
FIG. 6—Breathing exerciser, the first embodiment, the first scheme of the implementation of the throttling devices regulating the respiratory mixture composition FIG. 7—Breathing exerciser, the first embodiment, the second scheme of the implementation of the throttling devices regulating the respiratory mixture composition by the rectangular openings.

The adjustable throttling device 11, 12 installed in the channels 8 and 9 of communication the second chamber 2 with the atmosphere and with the third chamber 3 can be carried in form of the opening 18 cut in the housing of the second chamber 2 and in form of the sleeve 19 connected to the breathing bag 5 and mounted on the housing of the second chamber 2 to be moved along the opening 18 and partial overlap said opening 18. (FIG. 6).

While moving the sleeve 19 in one or another direction relatively to the opening 18 the passage sections of the opening 18, connecting the chamber 2 to the atmosphere and to the chamber 3, are changed in inverse proportion. Reducing the passage section of the opening 18, connecting the chamber 2 to the atmosphere, accompanies with increasing the passage section of the window 18, connecting the chamber 2 with chamber 3 and vice versa. Thus, only one control operation (movement of the sleeve 19 along the window 18) is carried out at the same time the adjustment of throttling devices 11 and throttling device 12, which is convenient when using this equipment, as well as increases the depth of control.

The adjustable throttle devices 11, 12, installed in the channels 8 and 9 of communication the second chamber 2 with the atmosphere and with the third chamber 3, can be carried out in the form of the sleeve 20 mounted on the housing 4 to be rotated about the longitudinal axis of the housing 4; the pair of the openings 21, 22 cut in the housing of the second chamber 2 and in the sleeve 20 on the portion located in the chamber 3; and the pair of openings 23, 24 cut in the housing of the second chamber 2 and in the sleeve 20 on the portion located outside the chamber 3. The openings 21, 22, 23, 24 are carried to overlap mutually of each other and to form when turning sleeve 20 the regulated in opposite directions passage sections, which communicate the second chamber 2 with the third chamber 3 and the third chamber 3 with the atmosphere. The openings 21, 22, 23, 24 may be carried out in rectangular (FIG. 7) or circular (FIG. 8) form.

Pairs of the openings 21, 22 and 23, 24 are carried to overlap of each other and to form their common passage sections, the magnitude of which is regulated by turning the sleeve 20. Herewith the increasing one pair of the passage sections is accompanied by the decreasing of the other passage sections.

Thus, one control operation with one unit (the rotation of the sleeve 20) provides at the same time the adjustment of the throttling device 11 and the adjustment of the throttling device 12, depending on the predetermined setting (decrease in the degree of choking in one throttling device with simultaneous increase in the degree of choking in the other), which provides ease of use exerciser and increases the depth of control of respiratory mixture.

The adjustable throttle devices 11, 12, installed in the channels 8 and 9 of communication the second chamber 2 with the atmosphere and with the third chamber 3, can be carried out in the form of the outer cup 25 and the located within said outer cup 25 inner cup 26 to rotate about the longitudinal axis and to contact by bottoms of the outer cup 25 and the inner cup 26; and containing the openings 27, 28 in the bottoms of the cups 25, 26 which are carried out to overlap mutually of each other and to form the regulated passage section, which communicates second chamber 2 with the third chamber 3 (the throttling device 12), and the openings 29 30 in the walls of cups 25, 26 which are carried to overlap mutually of each other and to form the regulated passage section, which communicates the second chamber 2 with the atmosphere (the throttling device 11), said openings 27, 28, 29, 30 are carried to change the passage sections value in the bottoms of the cups 25, 26, and the passage sections value in the walls of the cup 25, 26 in opposite directions when turning the inner cup 26 with the handle 31 (FIG. 9).

The openings 27, 28 may be carried out in the form of the sectors (FIG. 10), in the form of the circular opening (FIG. 11), in the form of slots (FIG. 12). It is possible the embodiment of a cup bottoms 25, 26 with two pairs of the openings 27, 28 (FIG. 13).

The openings 29, 30 may be carried out in the rectangular (FIG. 14) or circular (FIG. 15) forms. It is possible the embodiment of a cup side walls 25, 26 with two pairs of openings 29, 30 (FIG. 16).

When rotating the inner cup 26, the passage section of one of the throttling devices 11, 12 increases while as the passage section of the other of said throttling devices decreases. Thus, one control operation (movement of the handle 31 connected to the inner cup 26) is carried out at the same time the adjustment of the throttling devices 11, 12, which is convenient when using this equipment.

The adjustable throttle devices 11, 12 installed in the channels 8 and 9 of communication the chamber 2 with the atmosphere and with the chamber 3 may be carried out in the form of the three-way mixing valve K1 with two adjustable channels to reduce the respiratory mixture resistance in one of the regulated channels and at the same time to increase the respiratory mixture resistance in another regulated channel and vice versa via the single control handle P1 (FIG. 17).

Such valves are widely used for controlled mixing of the two flows of fluids. Schematic diagram of the crane shown in FIG. 18.

That is, the adjustable three-way mixing valve K1, which in this case functions as adjustable throttle devices 11, 12 installed in the channels 8 and 9 of communication the chamber 2 with the atmosphere and with the chamber 3, and only control handle P1 provide reducing of the respiratory mixture resistance in one of the adjustable throttling devices 11, 12 and at the same time increasing the respiratory mixture resistance in the other of said adjustable throttling device and vice versa thereby this embodiment increase the range of the respiratory mixture control and simplifies the exerciser using.

Figure 19:
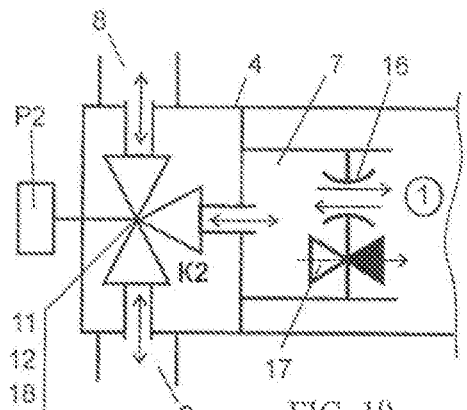
FIG. 19—Breathing exerciser, the first embodiment of the carrying out of the throttling devices in the form of three-way mixing valve with three regulated channels.
Figure 20:
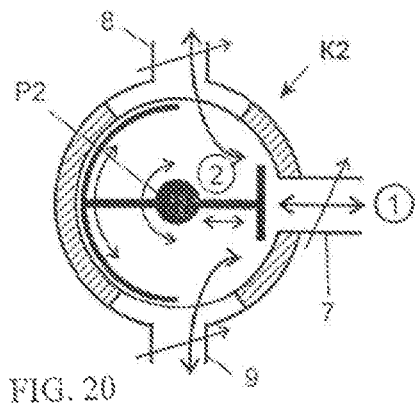
FIG. 20—Breathing exerciser, the first embodiment of the scheme of the implementation and operation of the three-way mixing valve with three adjustable channels.

The adjustable throttle device 11, 12, installed in the channels 8 and 9 of communication the second chamber 2 with the atmosphere and with the third chamber 3, and an adjustable throttling device 18 mounted in the canal 7 of communication the first chamber 1 and the second chamber 2 with each other, can be carried out in the form of the adjustable three-way mixing valve with three adjustable channels K2 carried out to reduce the respiratory mixture resistance in a regulated channels and to increase simultaneously the respiratory mixture resistance in the other regulated channel, and vice versa, and to regulate independently the respiratory mixture resistance in the third channel using a single control handle P2. It enables to regulate simultaneously and mutual oppositely the respiratory mixture resistance in the channels 8 and 9 of communication the second chamber 2 with the atmosphere and with the third chamber 3, and to regulate independently the respiratory mixture resistance in the channel 7 of communication the first chamber 1 and the second chamber 2 with each other. Such a solution is shown in FIG. 19. Schematic diagram of the mixing valve K2 is shown in FIG. 20.

In said mixing valve K2 the choking degree change of the breathing mixture flows in the channels 8, 9 is carried out by turning the control handle P2 in the horizontal plane and the choking degree change of the breathing mixture flow in the channel 7 is carried out by turning the control handle P2 in the vertical plane.

The execution of the adjustable throttling devices in the form of three-way mixing valve with two or three adjustable channels and of a single control handle provides ease and simplicity of its design and maintaining the wide regimes regulation opportunities at using the exerciser.

According to the second embodiment the breathing exerciser comprises three chambers communicating with each other: the first chamber 1, the second chamber 2, and the third chamber 3. The chambers 1, 2 are performed in the housing 4. The chamber 3 is carried out in the form of elastic breathing bag 5, which is connected to the housing 4. The chamber 1 is connected to the means 6 of connection the exerciser with the user's airways and communicates with the chamber 2 via two parallel channels 33 and 34. The chamber 2, in turn, communicates with the atmosphere via the channel 8 and with the chamber 3 through the channel 9.

The exerciser comprises the inhalation/exhalation resistance regulating means and respiratory mixture composition regulating means, installed in the channels communicating the chambers between each other and with the atmosphere.

The inhalation/exhalation resistance regulating means carried out in form of series-connected the adjustable throttling device 35 and the non-return check valve 36 installed in the channel 33, and in form of series connected the adjustable throttling device 37 and the non-return check valve 38 installed in the channel 34.

Figure 21:
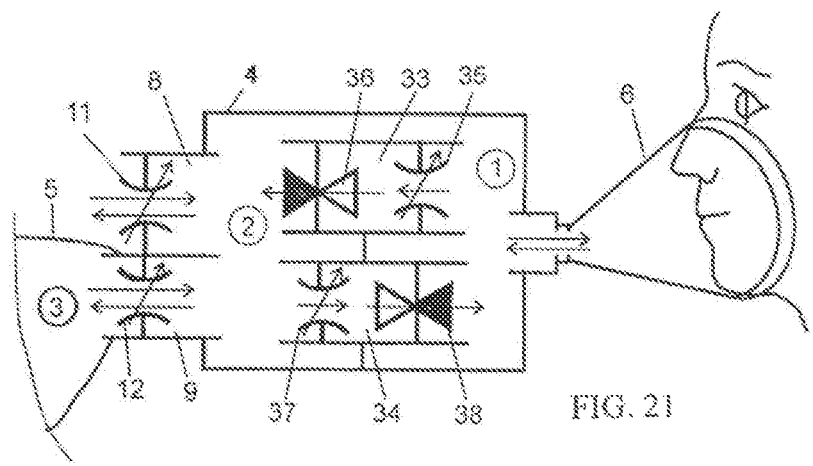
FIG. 21—Breathing exerciser, the second embodiment, the schematic diagram.

The respiratory mixture composition regulating means carried out in form of the adjustable throttling device 11 installed in the channel 8 of communication the chamber 2 with the atmosphere, and in form of the adjustable throttling device 12 installed in the channel 9 of communication the chamber 2 with the chamber 3. Non-return check valves 36, 38 are carried out to operate in reverse flow direction providing respiratory mixture passing through the channels 33, 34 in mutually opposite directions (FIG. 21).

When exhaling the enriched with carbon dioxide respiratory mixture fills the chamber 1 and then through the channel 33, wherein an adjustable throttling device 35 and the non-return check valve 36 are installed, enters the chamber 2. The one portion of the exhaled mixture releases from the chamber 2 into the atmosphere through the channel 8 and installed in said channel 8 the adjustable throttling device 11, the other portion of exhaled mixture through the channel 9 and installed in said channel 9 the adjustable throttling device 12 enters the chamber 3. The ratio of said exhaled mixture portions is set by the flow choking degree in the channels 8, 9 via the adjustable throttling devices 11 and 12.

When inhaling, the chamber 2 receives the atmospheric air through the channel 8 and installed in said channel 8 the adjustable throttling device 11 and the respiratory mixture of the elastic chamber 3 through the channel 9 and installed in said channel 9 the adjustable throttling device 12. The amount of the atmospheric air and the respiratory mixture of the chamber 3 entering the chamber 2 is set by the regulated throttling devices 11 and 12. The mixing of the atmospheric air and the respiratory mixture from the chamber 3 takes place in the chamber 2. The resulting respiratory mixture from the chamber 2 through the channel 34 and installed in said channel 34 the adjustable throttling device 37 and non-return check valve 38 enters the chamber 1, in which said mixture is further mixed with exhaled air and further supplied to the means 6, connecting the exerciser with the user's airways.

Thus, by the mixing the exhaled mixture with atmospheric air in the chamber 1 and continued mixing the resulting mixture with the exhaled air in the chamber 2 provides the respiratory mixture of given composition (the predetermined content of oxygen and carbon dioxide) supplied to the user's airways.

In the exerciser according to the second embodiment the respiratory mixture flow is separated in the channels 33, 34 (in the channel 33 there is the exhalation flow, in the channel 34 there is the inhalation flow) that provides the separate control of the respiratory mixture parameters of the inhalation and of the exhalation.

The breathing exerciser design according to the second embodiment provides the respiratory mixture composition control (the ratio of oxygen $O_2$ and carbon dioxide $CO_2$) which is given by the adjustable throttling devices 11, 12, and the separate and independent relation of the exhalation resistance with the adjustable throttling device 35 and the inhalation resistance with the adjustable throttling device 37.

Figure 22:
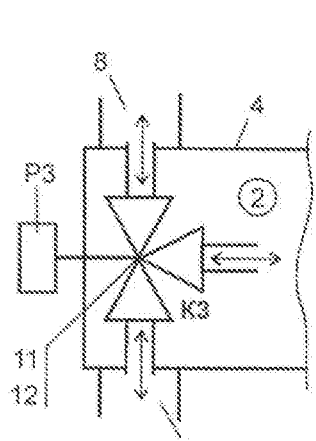
FIG. 22—Breathing exerciser, the second embodiment of the carrying out of the throttling devices regulating the respiratory mixture in the form of a three-way mixing valve with two regulated channels.

The adjustable throttling devices 11, 12, installed in the channels 8 and 9 of communication the chamber 2 with the atmosphere and with the chamber 3 may be carried out in form of the adjustable three-way mixing valve K3 with two regulated channels to reduce the respiratory mixture resistance in one of the regulated channels and at the same time to increase the respiratory mixture resistance in the other regulated channel, and vice versa, using a single control handle P3 (FIG. 22). Schematic diagram of the valve shown in FIG. 18.

In other words, the adjustable three-way mixing valve K3 in this case functions as the adjustable throttling device 11, 12, installed in the channels 8 and 9 of communication the chamber 2 with the atmosphere and with the chamber 3 with a single control mean—the handle P3.

The execution of the adjustable throttle devices 11, 12, in the form of the three-way mixing valve K3 with two adjustable channels and with the single control handle P3, increases the exerciser usability, simplifies its design while maintaining wide opportunities of the exerciser use regimes regulation.

Figure 23:
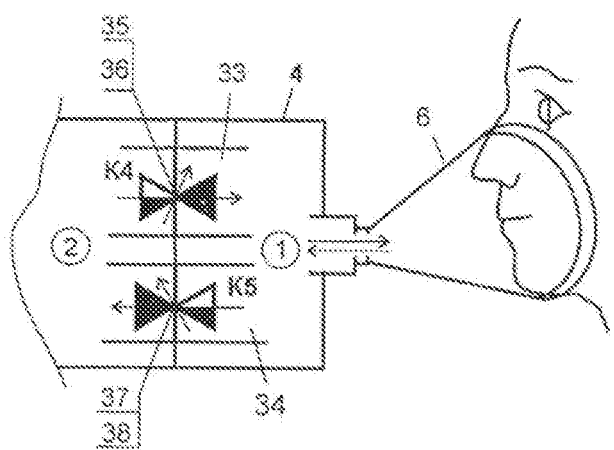
FIG. 23—Breathing exerciser, the second embodiment of the carrying out of the throttling devices regulating the inhalation/exhalation resistance in the form of the non-return check valves with means regulating the degree of the flow choking in the forward direction.

The series-connected adjustable throttling device 34 and the non-return check valve 35 installed in the channel 32 and also series-connected adjustable throttling device 36 and the non-return check valve 37 installed in the channel 33 may be carried out in the form of the non-return check valves K4, K5 with means for regulating the degree of choking the flow in the forward direction (FIG. 23).

Throttling means regulating the degree of the flow choking may be carried out in the form of the adjustable stop limiting the amount of movement of the locking element in the direction of valve opening. FIG. 24, 25 show possible arrangements of the valves (FIG. 24 shows the ball non-return check valve, FIG. 25 shows flap non-return check valve).

This design is one of the possible implementation of the means regulating the inhalation/exhalation resistance in the exerciser according to the second embodiment of our invention.

Breathing exerciser according to the second embodiment may be configured as following.

The housing 4 is carried out in the form of the cylinder with the transverse partition 39. On both sides of the partition 39 inside the housing 4 the cups 40, 41 are installed to be rotated. The cup bottoms 42, 43 contact with the partition 39. The cups 40 and 41 installed in the housing 4 are rotated by the handles 44 which move in the slots carried out the housing 4 (FIG. 26).

In the partition 39 the diametrically opposite openings 45, 46 (FIG. 28) are made. In the bottom 42 of the cup 40 the opening 47 and diametrically opposite to said opening 47 the circular groove 48 are performed. The opening 47 on the inner side the cup 40 is overlapped by the flap or petal non-return check valve 49 (FIG. 27). In the bottom 43 of the cup 41 the opening 50 and diametrically opposite to said opening 50 the circular groove 51 are exercised. The opening 50 on the inner side of the cup 41 is overlapped by the flap or petal non-return check valve 52 (FIG. 29).

The groove 51 and the opening 50 in the bottom 43 of the cup 41 are made diametrically opposite in relation to the groove 48 and the opening 47 in the bottom 42 of the cup 40. The groove 48 in the bottom 42 of the cup 40, the opening 45 in the partition 39 and the opening 50 in the bottom 43 of the cup 41 with the valve 52 are arranged coaxially. The opening 47 in the bottom 42 of the cup 40 with the valve 49, the opening 46 in the partition 39 and the groove 51 in the bottom 43 of the cup 41 are also arranged coaxially.

In this embodiment, the partition 39, the cups 40, 41 with the opens and grooves the petal valves, performed the above manner, serve as the channels 33, 34, the adjustable throttling devices 35, 37 and the non-return check valves 36, 38 shown in FIG. 21 (a schematic diagram of the exerciser according to the second embodiment).

Figure 7:
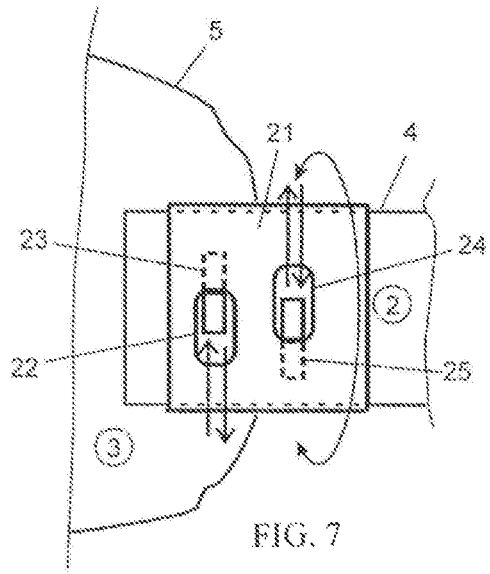
Figure 8:
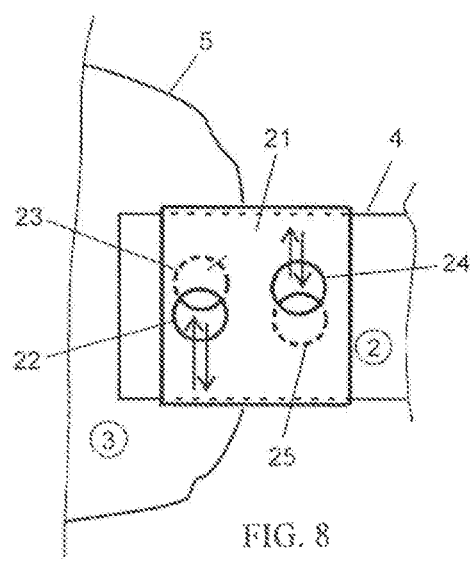
FIG. 8—Breathing exerciser, the first embodiment, the second scheme of the implementation of the throttling devices regulating the respiratory mixture composition by the circular openings.

The adjustable throttling devices 11, 12, as in the first embodiment, can be performed according to schemes shown in FIGS. 6-8, or by using the inner cup in the schemes in FIG. 9-16, or using or the three-way mixing valve according to the schemes shown in FIGS. 17, 18 (the first embodiment).

When exhaling, the flap or petal valve 51 is closed the flap or petal valve 49 is open. The respiratory mixture, enriched in carbon dioxide, fills the chamber 1, and further, through the groove 51 in the bottom 43 of the cup 41 and through the opening 46 in the partition 39, through the opening 47 in the bottom 42 of the cup 40 and through the open valve 79 enters the chamber 2. The part of the exhaled mixture from the chamber 2 is released into the atmosphere through the channel 8 and, installed in said channel 8, the adjustable throttling device 11, the rest part of the exhaled mixture through the channel 9 and installed in said channel 9 the adjustable throttling device 12 is supplied into the elastic chamber 3. The ratio of said exhaled mixture parts is given by the choking degree of the flows in the channels 8,9 via the adjustable throttling devices 11, 12.

The regulation of the exhalation resistance is performed by turn the cup 40, causing changes in one or another side the flow section formed by the opening 46 in the partition 39 and the opening 47 in the bottom 42 of the cup 40 as a result of their mutual displacement.

When inhaling the flap or petal valve 52 is open, the flap or petal valve 49 is closed. The atmospheric air flows into the chamber 2 through the channel 8 and, installed in said channel 8, the adjustable throttling device 11, and the respiratory mixture of an elastic chamber 3 enters said chamber 2 through the channel 9 and, installed in said channel 9, the adjustable throttling device 12. The amount of the atmospheric air and the breathing mixture from the chamber 3, entering the chamber 2, is given by the adjustable throttling devices 11 12. The agitation of the ambient air with the respiratory mixture from the chamber 3 occurs in the chamber 2.

The respiratory mixture from the chamber 2 through the slot 48 in the bottom 42 of the cup 40, through the opening 45 in the partition 39, through the opening 50 in the bottom 43 of the cup 41, through the open petal valve 52 flows into the chamber 1, and then into the user's respiratory system.

The inhalation resistance regulation is performed by turn the cup 41, causing changes in one or another side the flow section formed by the opening 45 in the partition 39 and the opening 50 in the bottom 43 of the cup 41 at their mutual displacement.

Figure 30:
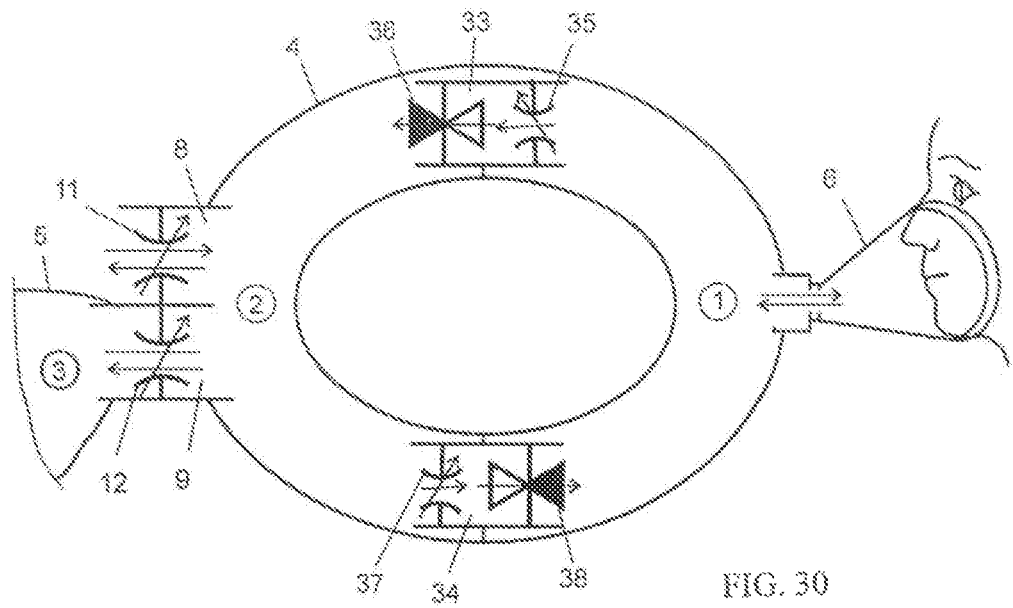
FIG. 30—Breathing exerciser, the second embodiment, an example of execution of the housing.

The housing 4 may be carried out in the form of the hollow ring, the cavity of which is divided into chambers 1, 2, communicating with each other. In the channels 33 and 34 of chambers 1, 2 are installed the adjustable throttling device 35 and the non-return check valve 36, the adjustable throttling device 37 and the non-return check valve 38, respectively (FIG. 30).

According to the third embodiment, the breathing exerciser comprises three chambers communicating with each other: the first chamber 1, the second chamber 2 and the third chamber 3. The chamber 1 and the chamber 2 are located in the housing 4. The chamber 3 is carried out in the form of the elastic breathing bag 5, which is connected to the housing 4. The chamber 1 is communicated with the means 6 connecting the exerciser to the user's respiratory tract. The second chamber 2 is divided into two cavities 2a and 2b. The cavity 2a communicates with the chamber 1 through the channel 53, with the atmosphere through the channel 54 and with the chamber 3 through the channel 55. The cavity 2b communicates with the chamber 1 through the channel 56, with chamber 3 through the channel 57 and with the respiratory mixture source 58 via the channel 59.

The exerciser contains the means regulating respiratory mixture composition and inhalation/exhalation resistance installed in the channels of communication the chambers with each other and with the atmosphere.

Figure 31:
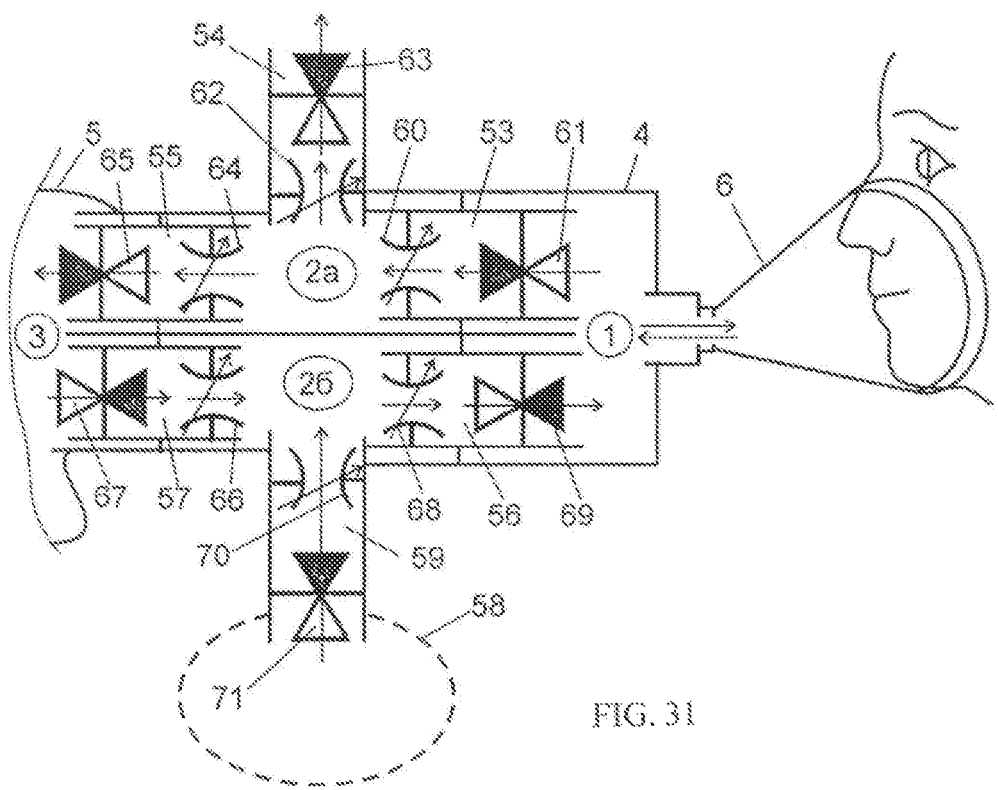
FIG. 31—Breathing exerciser, the third embodiment, the schematic diagram.

Said means are carried out in the form of in-series connected the adjustable throttling device 60 and the non-return check valve 61, installed in the channel 53 of communication the cavity 2a with the chamber 1 in the flow direction towards the cavity 2a; in the form of in-series connected the adjustable throttling device 62 and the non-return check valve 63, installed in the channel 54 of communication the cavity 2a with the atmosphere in the flow direction towards the atmosphere; in the form in-series connected the adjustable throttling device 64 and the non-return check valve 65, installed in the channel 55 of communication the cavity 2a with the chamber 3 in the flow direction towards the chamber 3; in the form of in-series connected the adjustable throttling device 66 and the non-return check valve 67, installed in the channel 57 of communication the chamber 3 with the cavity 2b in the flow direction towards the cavity 2b; in the form of in-series connected the adjustable throttling device 68 and the non-return check valve 69, installed in the channel 56 of communication the cavity 2b with the chamber 1 in the flow direction towards the chamber 1; in the form of in-series connected the adjustable throttling device 70 and the non-return check valve 71, installed in the channel 59 of communication the cavity 2b with the respiratory mixture source 58 in the flow direction towards the cavity 2b (FIG. 31).

While exhaling the enriched in carbon dioxide respiratory mixture, fills the chamber 1 and then through the channel 53 and trough installed in said channel 53 the adjustable throttling device 60 and the check valve 61 enters the cavity 2a. The part of the respiratory mixture from the cavity 2a through the channel 54 and through installed in said channel 54 the adjustable throttling device 62 and the non-return check valve 63 is released into the atmosphere. Another part of the respiratory mixture from the cavity 2a through the channel 55 and through the installed in said channel 55 the adjustable throttling device 64 and the check valve 65 enters the elastic chamber 3. The ratio of these respiratory mixture parts by the adjustable throttling devices 62, 64. The exhalation resistance is regulated with the throttling device 60.

When inhaling, the cavity 2b accepts the respiratory mixture from the chamber 3 through the channel 57 and through installed in said channel 57 the adjustable throttling device 66 and the non-return check valve 67 as well as from the respiratory mixture sours 58 through the channel 59 and installed in said channel 59 the adjustable throttling device 70 and the non-return check valve 71. The amount of the respiratory mixture, entering the cavity 2b from the chamber 3 and from the respiratory mixture source 58 is given by the adjustable throttling devices 66, 70. In the cavity 2b the respiratory mixture flows, entering said cavity 2b from the chamber 3 and from the respiratory mixture source 58, are mixing. From the cavity 2b the respiratory mixture through the channel 56 and trough installed in said channel 56 the adjustable throttling device 68 and the non-return check valve 69 enters the chamber 1, wherein additionally agitates with the air mixture previously exhaled, and further is supplied to the exerciser means 6 connecting the exerciser to the users airways. Hence, the respiratory mixture of given composition is supplied to the user's airways as a result of the agitating of the respiratory mixtures in the cavity 2b and in the chamber 1.

The inhalation resistance is regulated with throttling device 68. The composition of the respiratory mixture composition is set with the adjustable throttle devices 66, 70.

Such an execution of the breathing exerciser provides the separate and independent regulation of the inhalation resistance and the exhalation resistance with the adjustable throttling devices 68 and 60; the regulation of the respiratory mixture composition with the adjustable throttle devices 66 and 70; the separation of respiratory mixtures on two flows, the exhaled mixture flows through the channel 53 and the cavity 2a, the inhaled mixture passes through the cavity 2b and the channel 56; the using of the atmospheric air as the breathing substance and using of the particular breathing mixtures with special additives, which are obtained in the respiratory mixture source 58.

Figure 32:
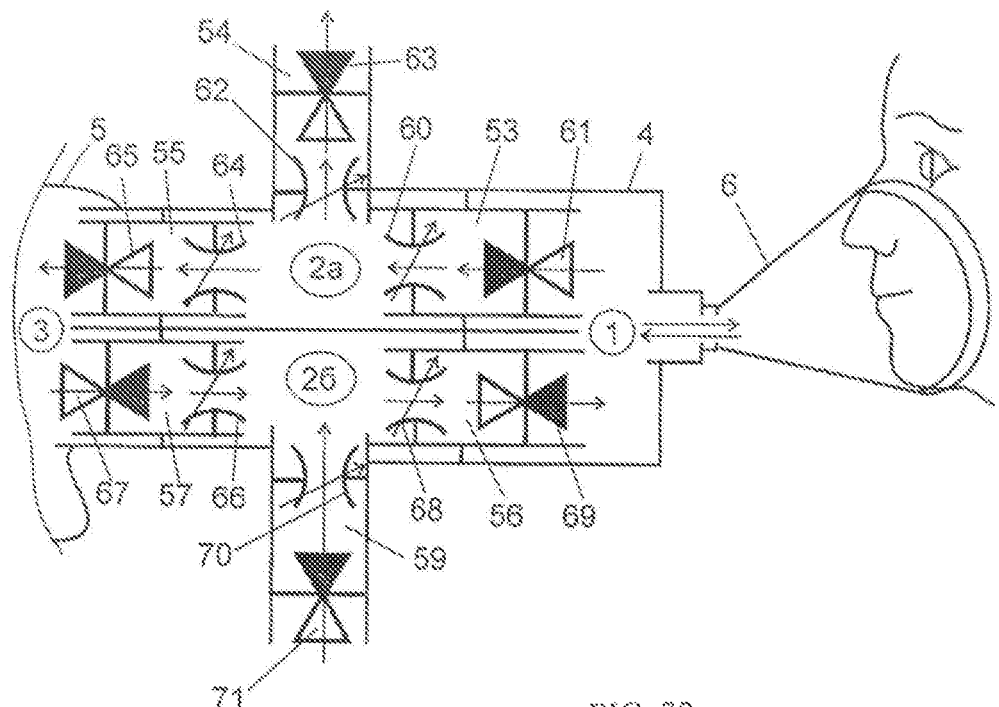
FIG. 32—Breathing exerciser, the third embodiment, the respiratory mixture source is atmosphere.

As the source of breathing air the atmosphere can be used. In this case, the cavity 2b communicates directly with the atmosphere through the channel 58, in which the adjustable throttling device 70 and the non-return check valve 71 in the flow direction towards the cavity 2b (FIG. 32).

Figure 33:
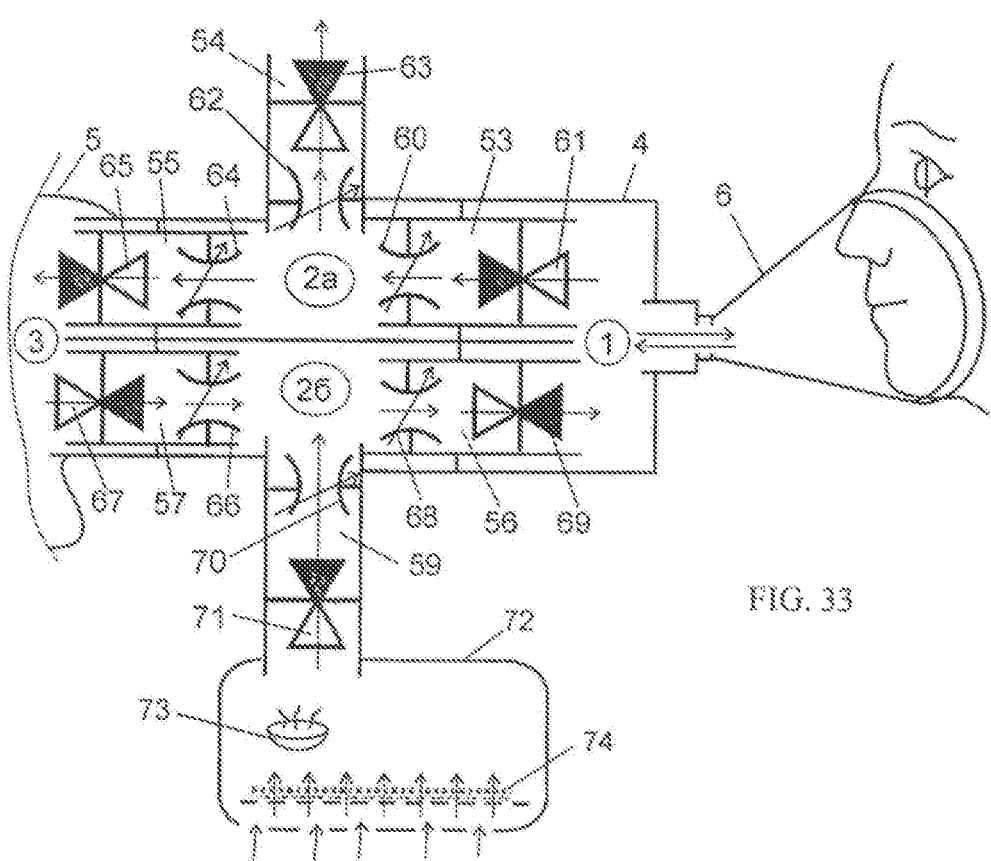
FIG. 33—Breathing exerciser, the third embodiment, the respiratory mixture source is the chamber for preparation the respiratory mixture.

The source of the breathing mixture 58 may be carried out in form of the respiratory mixture preparation chamber 72, which communicates with atmosphere and has the cavity for natural or synthetic oils and/or herbal extracts 73 and/or herbs and/or mineral substances 74, for example, therapeutic mineral salts with heating means or without them (FIG. 33).

Such an execution increases the health benefits of the exerciser using as a result of the presence of the breathing mixture treatment additives.

Figure 34:
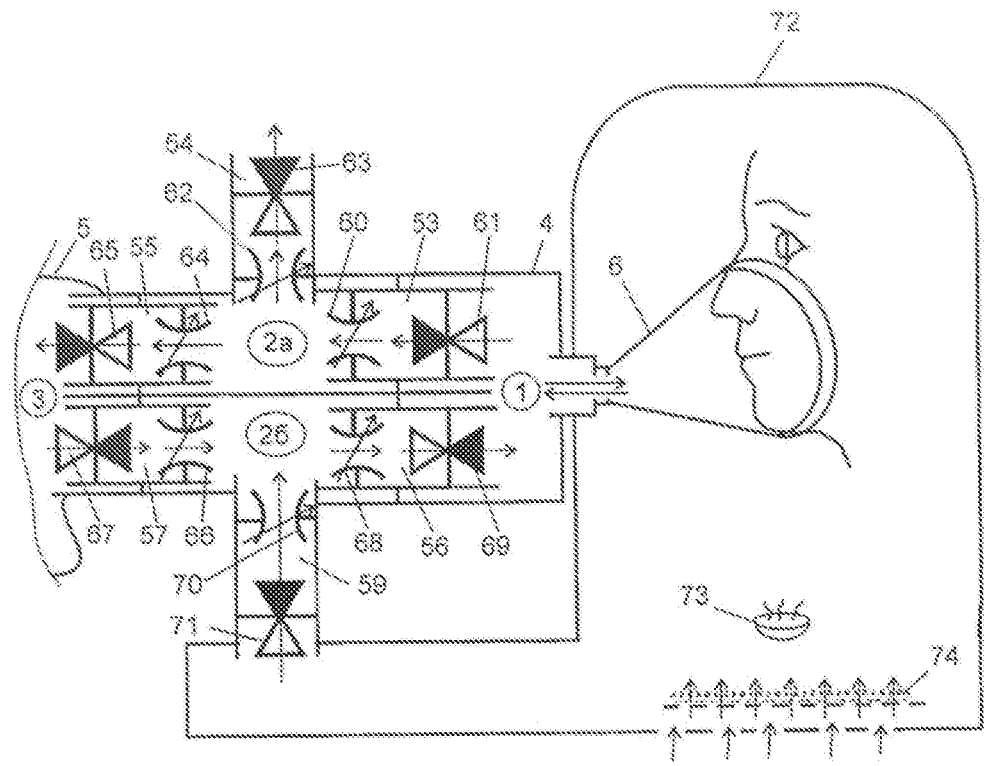
FIG. 34—Breathing exerciser, the third embodiment, the chamber for preparation the respiratory mixture carried out to locate the part of the user's body.

The respiratory mixture preparation chamber 72 can be adapted to accommodate therein a user or part of him, e.g., the user's head (FIG. 34).

With this arrangement, medical additives present in the breathing mix, not only act on the respiratory and on exposed areas of the body by further improving effect increases.

Figure 35:
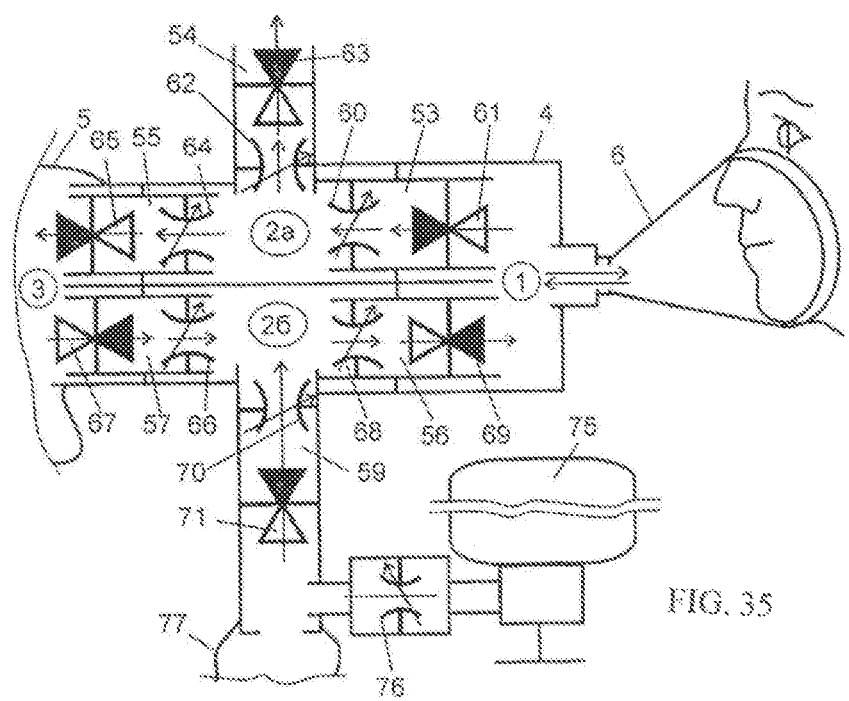
FIG. 35—Breathing exerciser, the third embodiment, the respiratory mixture source is the irrespective LPG device.

The source of breathing mixture may be formed as an independent source of breathing gas, such as LPG device 75 with the adjustable throttling device 76 and breathing bag 77 (FIG. 35).

With this arrangement, a gas mixture used in the exerciser does not depend on the environmental conditions.

Figure 36:
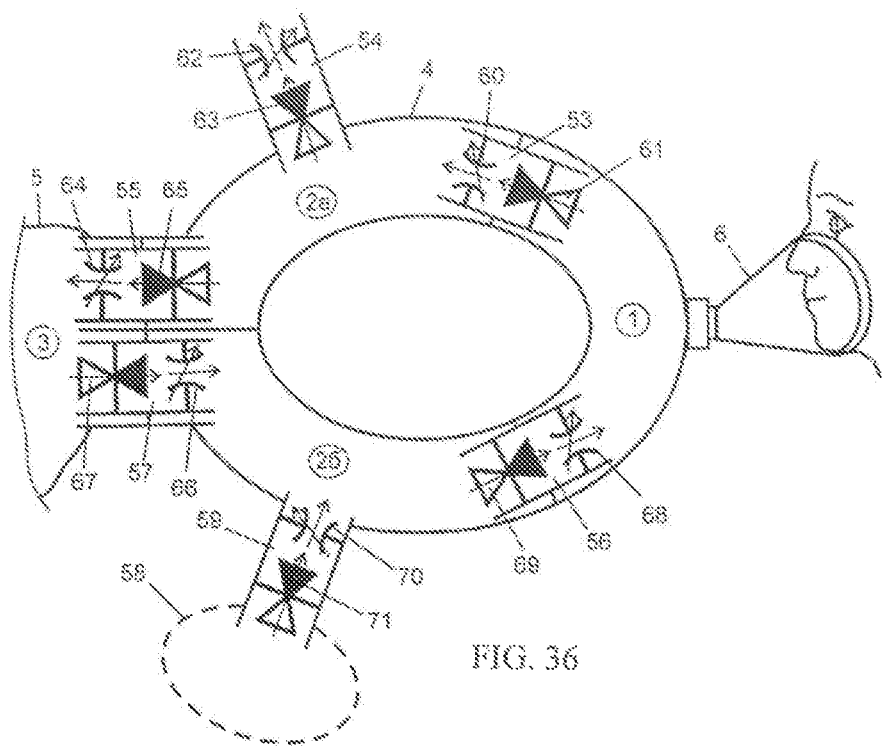
FIG. 36—Breathing exerciser, the third embodiment, an example of execution of the house.

In the exerciser according to the third embodiment, the housing 4 can be configured as a hollow ring, the cavity of which is divided into the first chamber 1, the cavities 2a, 2b of the second chamber, which communicate with each other by the channel 53 with the adjustable throttling device 60 and the non-return check valve 61 as well as the channel 56 with the adjustable throttling device 68 and the non-return check valve 69 (FIG. 36). This solution is the example of the possible implementation of the housing 4 of a third embodiment of the exerciser.

Figure 37:
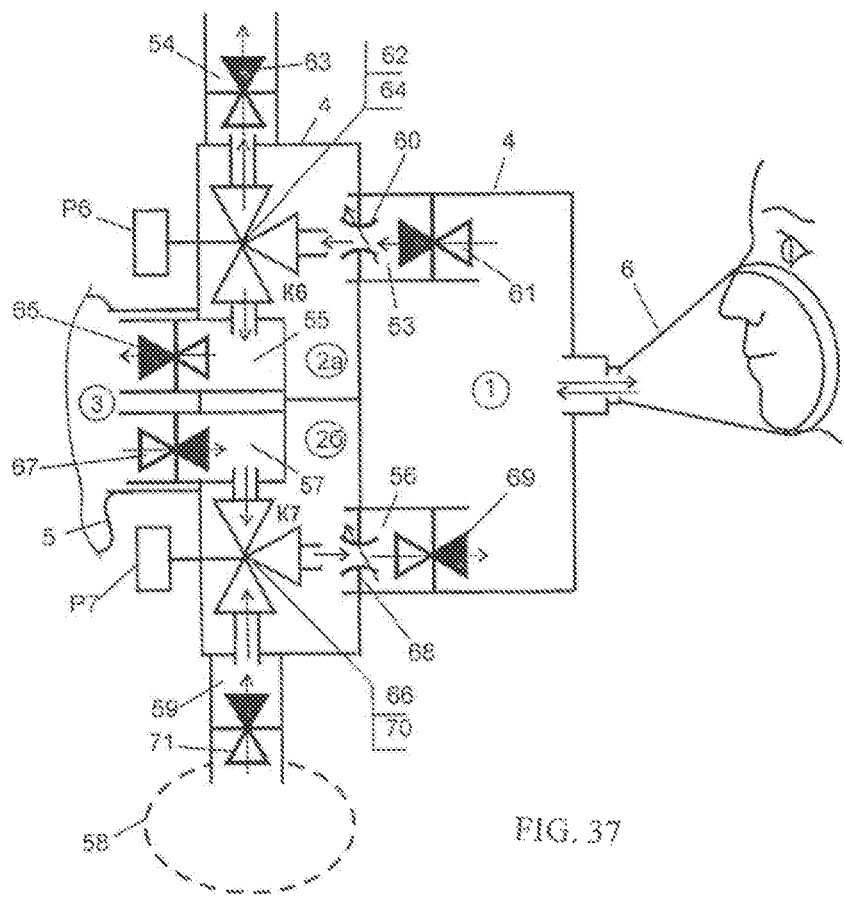
FIG. 37—Breathing exerciser, the third embodiment of carrying out the throttling devices in the form of three-way mixing valves with two regulated channels.

In the exerciser according to the third embodiment, the adjustable throttle devices 62, 64, installed in the channels 54, 55, and the adjustable throttle device 66, 70, installed in the channels 57, 59, may be carried out in form of the regulated three-way mixing valve K6, K7 with two regulated channels to reduce the respiratory mixture resistance in one of the regulated channels and simultaneously to increase the respiratory mixture resistance in the other regulated channel, and vice versa, using the control handles P6, P7 (FIG. 37). Schematic diagram of such valves is shown FIG. 18 (the first embodiment of the simulation).

That is, in this case the adjustable three-way mixing valve K6 functions as adjustable throttle devices 62, 64, installed the channels 54, 55, with the single control handle P6, and the adjustable three-way mixing valve K7 serves as the adjustable throttling devices 66 and 70, installed in the channels 57, 59, with the single control handle P7. The valve regulation is achieved by turning the control handles P6, P7 in the horizontal plane. For example, when turning the tap handle P6 of the valve K6 in either direction in horizontal plane the characteristics of the throttling devices 62, 64 are changed on the feedback dependence (when increasing the flow resistance in one direction the flow resistance in the other direction is decreased, and vice versa).

Figure 38:
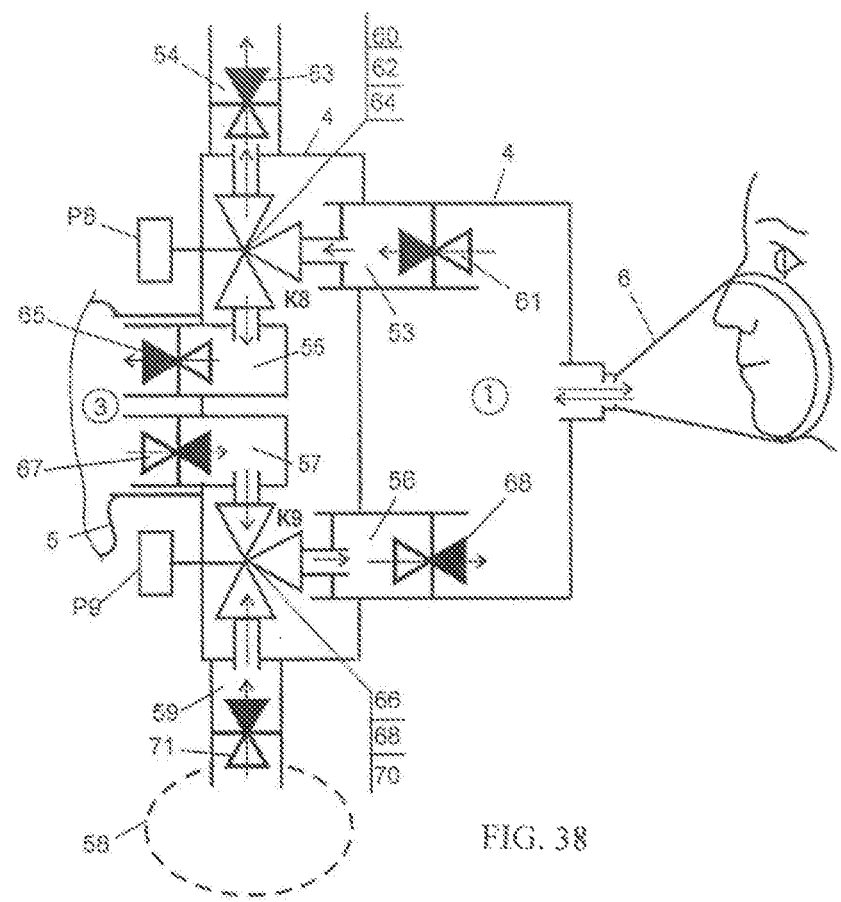
FIG. 38—Breathing exerciser, the third embodiment of the carrying out the throttling devices in the form of three-way mixing valve with three regulated channels.

In the exerciser according to the third embodiment, the adjustable throttling devices 60, 62, 64, installed in the channels 53, 54, 55, and the adjustable throttling devices 66, 68, 70, installed in the channels 57, 56, 59, may be carried out in the form of the three-way adjustable mixing taps K8, K9 with three adjustable channels to reduce the breathing mixture resistance in one regulated channel while to increase the respiratory mixture resistance in the other regulated channel, and vice versa, as well as the independent regulation the breathing mixture resistance in the third channel with the combined control handles P8, P9 (FIG. 38). The schematic diagram of such taps is shown in FIG. 20 (the first embodiment of the exerciser).

That is, in this case the adjustable three-way mixing tap K8 serves as the adjustable throttling devices 60, 62, 64, installed in the channels 53, 54, 55 with the single control handle P8 and the adjustable three-way mixing tap K9 serves as the adjustable throttling devices 66 68, 70 installed in the channels 57, 56, 59 with the single control handle P9. The regulation of these taps is achieved by turning the control handles P8, P9 in the horizontal and vertical planes. For example, when turning the handle P8 of the tap K8 in either direction in the horizontal plane, the characteristics of the throttling devices 62, 64 are changed on the feedback dependence (when increasing the flow resistance in one regulated channel the flow resistance in the other regulated channel is decreased, and vice versa). The turning of the handle P8 of the tap K8 upwards or downwards in a vertical plane is accompanied with the characteristics changing of the throttle device 60.

The execution of the adjustable throttling devices in the form of three-way mixing taps with two or three regulated channels with a single control handle provides ease of the exerciser using, simplicity of its design while maintaining the wide capacity of the regimes regulation when using the exerciser.

Figure 39:
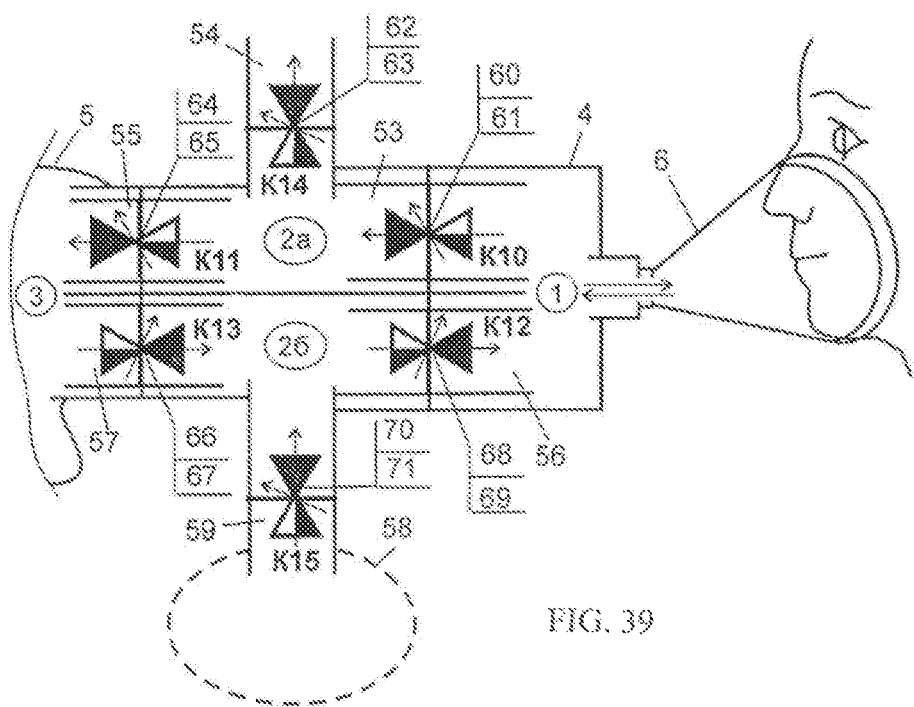
FIG. 39—Breathing exerciser, the third embodiment of the carrying out the throttling devices in form of the non-return check valves with means regulating the degree of the flow chocking in the forward direction.

According to the third embodiment of the exerciser, the serially connected adjustable throttling devices and check valves 60 and 61, 62 and 63, 64 and 65, 66 and 67, 68 and 69, 70 and 71, installed respectively in the channels 53, 54, 55, 57, 56, 59 of the exerciser, can be carried out in the form of the non-return check valves K10, K11, K12, K13, K14, K15 with means regulating the degree of choking the flow in the forward direction; said means may be carried out in the form of the adjustable stop to limit the amount of movement of the closing element in the valve opening direction (FIG. 39).

Such possible valve schemes are illustrated in FIGS. 24, 25 (the second embodiment of the exerciser, in FIG. 24 is shown the ball check valve, in FIG. 25 is shown the flap check valve).

In this case, the adjustable non-return check valve K10 puts into effect the function of the throttling device 60 and the non-return check valve 61, the adjustable non-return check valve K14 executes the function of the throttling device 62 and the check valve 63, the adjustable non-return check valve K11 functions as the throttling device 64 and the non-return check valve 65, the adjustable non-return check valve K13 performs the function of the throttling device 66 and the non-return check valve 67, the adjustable non-return check valve K12 realizes the function of the throttling device 68 and the non-return check valve 69, the adjustable non-return check valve K15 serves as the throttling device 70 and the non-return check valve 71.

Such a solution is yet another possible implementation example of regulation means of the breathing mixture composition and inhalation/exhalation resistance of the third embodiment of my invention.

The breathing exerciser according to the third embodiment may be configured as follows.

Figure 40:
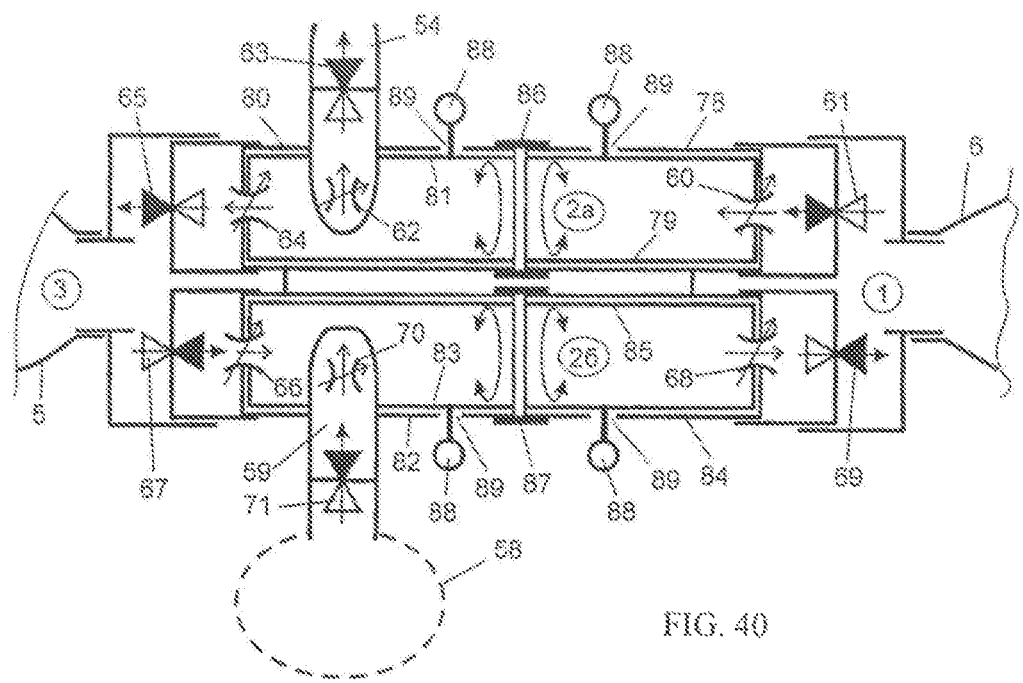
FIG. 40—Breathing exerciser, the third embodiment, the example of carrying out the throttling device in the form of cups.

Each of adjustable throttling device 60, 62, 64, 66, 68, 70 may be carried out in form of the pair cylindrical cups—the outer cup and inner cup, said inner cup is installed in said outer cup to be rotated (FIG. 40).

The cup bottoms are in contact to each other. The walls of the inner and outer cups are also in contact with each other. In the bottoms, side walls glasses cut The openings in the cup bottoms and in the cup walls are configured as to overlap each other and consequently changes the total flow section while rotating of the inner cup in one or another direction (change in the degree of choking).

The possible schemes of perform such throttling device are shown in FIGS. 9-16 (the first embodiment of offered exerciser).

In this way, the bottoms of said cups 78, 79 are configured in the adjustable throttle device 60. The bottoms of cups 80, 81 form the adjustable throttle device 64. The openings in the side walls of the cup 80, 81 are the adjustable throttle device 63. The openings in the side walls of the cups 82, 83 form the adjustable throttle device 70, and the openings in the bottoms of said cup represent the adjustable throttling device 66. The openings in the bottoms of the cups 84, 85 form the adjustable throttle device 68. The open ends of the outer cups 78, 80 and 82, 84 are connected by the annular collars 86, 87 respectively.

The rotation of the inner cup is performed by the handles 88 which move in the openings 89 formed in the outer cups 78, 80, 82, 84. The turning of the inner cup 81 changes the choking degree carried out by the throttling devices 62, 64 in mutually opposite directions, the turning inner cup 83 changes the choking degree carried out by the throttling devices 66, 70 in mutually opposite directions. That is, the throttling devices 62, 64 control is carried out with the only control operation (rotating the cup 81) at the same time. The throttling devices 66, 70 control is carried out similarly (rotating the cup 83).

In any of the embodiment of the invention, the sensors 90, such as the breathing mixture pressure sensor and/or respiratory mixture composition sensor and/or mixture flow rate sensor, can be installed in at least one of the chambers (channels) and carried out with visualization means 91 to read out said sensors 90 data and visualize to the user the information about the operating exerciser modes.

Figure 41:
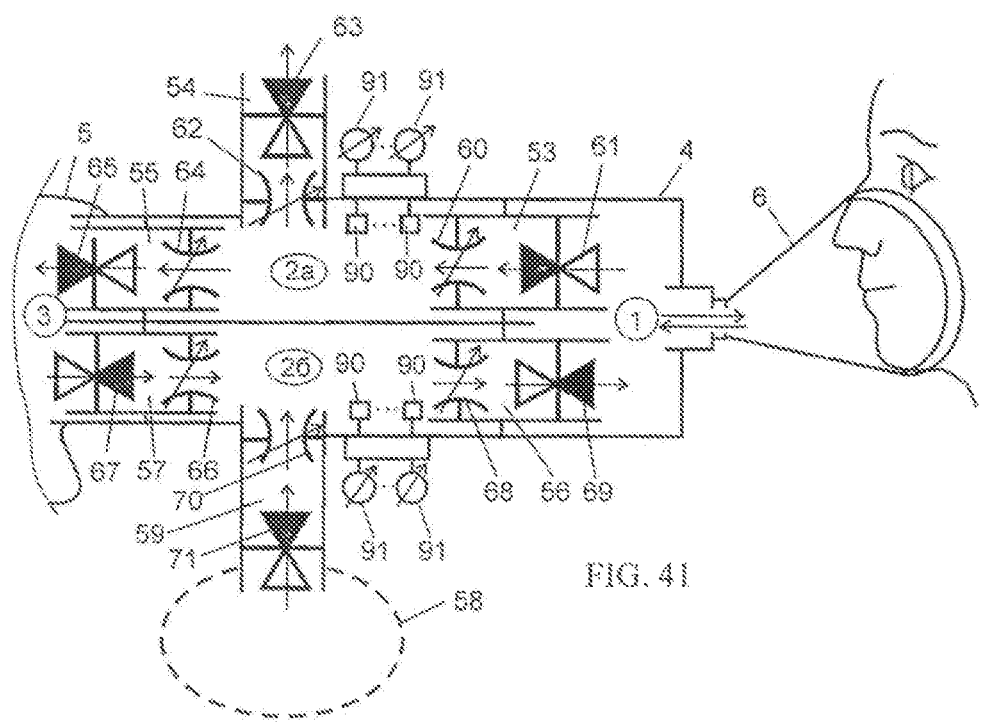
FIG. 41—Breathing exerciser, the first, second and third embodiment, the carrying out of the exerciser with the sensors of the respiratory mixtures parameters.

FIG. 41 shows an exemplary sensors 90 arrangement including visualization means 91 representing the sensors' 90 readings concerning to the third embodiment of the exerciser. Sensors 90 are located in the cavities 2a and 2b of the second chamber, through which the respiratory mixture of inhalation and exhalation flows, respectively.

This allows the user to control the parameters of respiratory mixture inhalation and respiratory mixture exhalation separately and correct independently the operating exerciser mode via the adjustable throttling devices 60, 62, 64, 66, 68, 70.

Any embodiment of the exerciser may be configured integrally the computer system controlling the operating exerciser mode and including the sensors 90 of the respiratory mixture pressure and/or respiratory mixture composition and/or mixture flow rate, installed in at least one of the chambers (channels); the processor 92 with predetermined operating mode algorithms of the exerciser; the monitor 93 visually presenting the exerciser mode information to the user; the input unit 94 connected to said sensors 90 and processor 92; and output unit 95 connected with the means controlling the adjustable throttling devices and with the processor 92.

Figure 42:
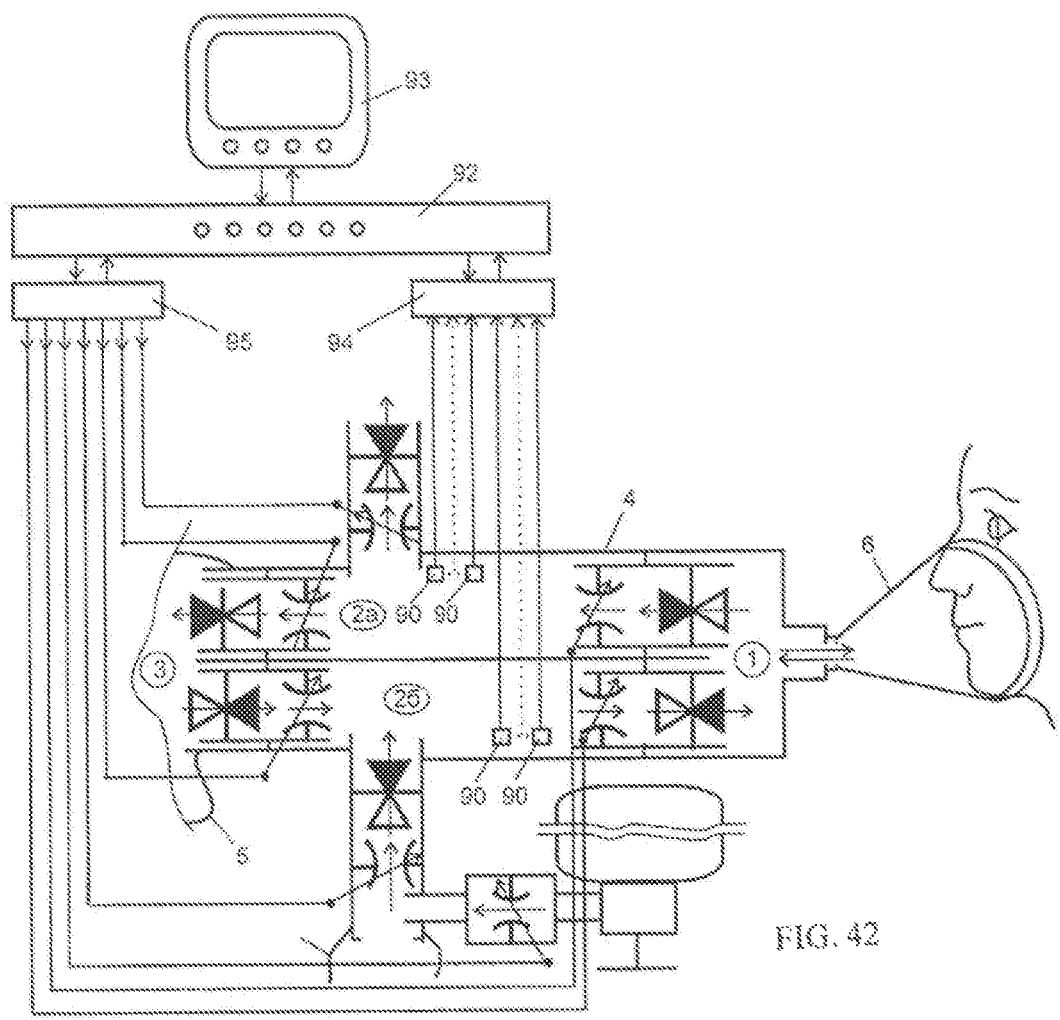
FIG. 42—Breathing exerciser, the first, second and third embodiment, the example of the carrying out the exerciser with the computer system controlling the operating mode.

FIG. 42 shows an example of the exerciser with the computer system controlling the operating mode of the third embodiment. Sensors 81 are located in the second chamber cavities 2a and 2b, through which the exhaled respiratory mixture and the inhaled respiratory mixture flow, respectively.

According to any embodiment of the invention, the first chamber 1 can be provided with at least one partition, dividing said chamber into at least two cavities (chamber) and possessing at least one voice strap, mounted on said partition, and at least one voice tab, inflicted on said strap.

Figure 43:
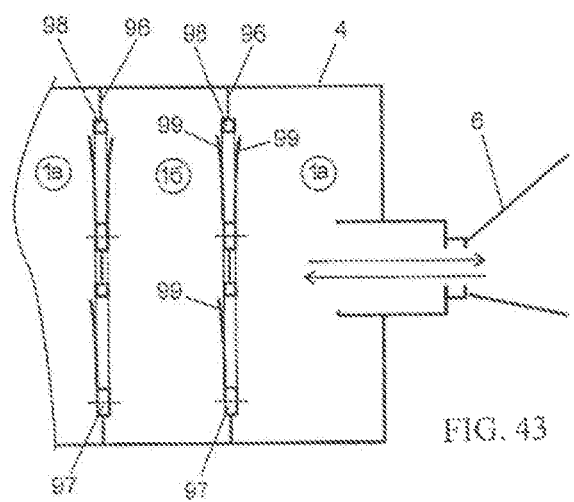
FIG. 43—Breathing exerciser, the first, second and third embodiment, the example of carrying of the chamber with voice tabs.

FIG. 43 shows an example of exerciser implantation including the first chamber 1 with two partitions 96 dividing the chamber 1 into three cavities (chamber)—1a, 1b, 1c. Each partition 96 includes mounted on it voice straps 97, 98 with one tongue 99 (voice straps 97) and with two tongues 99, (voice strap 98). The cavities 1a, 1b, 1c are the resonators, providing the increasing the amplitude of the sound waves generated by voice tongues 99.

Such an arrangement provides the generation in the respiratory mixture near the human respiratory tract acoustic vibrations of a given frequency, the dynamic effect of which on the respiratory increases health effects on the exerciser user.

In either embodiment, the means for connecting the exerciser to the user's airways can be carried out in the form of the sealed facial mask 6, or the tube with the mouthpiece, or the hermetic helmet or the airtight suit (not shown).

In any of the embodiment of the invention, means regulating the respiratory mixture composition and the inhalation/exhalation resistance function as:
- control the choking degree of respiratory mixture flow (creation of controlled breathing gas flow obstructions);
- mixing the respiratory mixture flows for obtaining the respiratory mixture of given composition.
- separation the respiratory mixture flows of inhalation and exhalation;
- preparation of the respiratory mixture of given composition.

The invention claimed is:

1. A breathing exerciser comprising a first chamber connected with a means for connecting the exerciser to an exerciser user's airways, a second chamber in communication with the first chamber, a third chamber in communication with the second chamber, a means for regulating a respiratory mixture composition, a means for regulating inhalation resistance and exhalation resistance installed in a channel of communication of the first chamber with the second chamber, wherein the second chamber is configured to communicate with an atmosphere, the third chamber is made from elastic material, the means for regulating the respiratory mixture composition comprises an adjustable throttling device, installed in a channel communicating the second chamber with the third chamber, and a controlled throttling device, installed in a channel of communication of the second chamber with the atmosphere, and the means for regulating the inhalation resistance and the exhalation resistance is configured to regulate the inhalation resistance and the exhalation resistance separately and independently.

2. The breathing exerciser according to claim 1, wherein the means for regulating the inhalation resistance and the exhalation resistance comprises an adjustable throttling device with a locking element installed in a flow passage section of said throttling device to move in opposite directions relative to a direction that is perpendicular to flow through said flow passage section and adjustable stops limiting said movement in opposite directions.

3. The breathing exerciser according to claim 2, wherein the adjustable throttling device locking element comprises a console petal to deflect elastically in the opposite directions.

4. The breathing exerciser according to claim 2, wherein the adjustable throttling device locking element comprises a freely established spherical ball.

5. The breathing exerciser according to claim 1, wherein the means for regulating the inhalation resistance and exhalation resistance comprises a parallel-connected check valve and adjustable throttling device, and also one more adjustable throttling device connected in series with said parallel-connected check valve and adjustable throttling device.

6. The breathing exerciser according to claim 5, wherein the non-return check valve is configured to allow flow towards the first chamber.

7. The breathing exerciser according to claim 5, wherein the non-return check valve is configured to allow flow towards the second chamber.

8. The breathing exerciser according to claim 1, wherein the adjustable throttling device and the controlled throttling device, installed in the channels communicating the second chamber with the atmosphere and with the third chamber, comprise an opening cut out in a second chamber housing and a sleeve hermetically connected with the third chamber and mounted on the second chamber housing to be moved along said opening.

9. The breathing exerciser according to claim 1, wherein the adjustable throttling device and the controlled throttling device, installed in the channels of communication of the second chamber with the atmosphere and with the third chamber comprise a sleeve mounted on a second chamber housing to rotate about a longitudinal axis of said housing, a set of openings cut out in the second chamber housing and in a sleeve portion located within the third chamber, and a set of openings cut out in the second chamber housing and in a sleeve portion located outside the third chamber, wherein one opening of each set of openings is configured to be overlapped with another opening of the same set.

10. The breathing exerciser according to claim 1, wherein the adjustable throttling device and the controlled throttling device, installed in the channels of communication of the second chamber with the atmosphere and with the third chamber, comprise an outer cup and, installed within said outer cup, an inner cup to rotate around a longitudinal axis and wherein a bottom of the inner cup contacts a bottom of the outer cup, cut outs in both cup bottoms to be mutually overlapped and to form an adjustable flow section communicating the second chamber with the third chamber, and cut outs in both cup walls to be mutually overlapped and to form an adjustable flow section communicating the second chamber with the atmosphere, said cut outs configured to change values of flow cross sections in said both cup bottoms and values of flow cross sections in said both cup walls when turning the inner cup in opposite directions.

11. The breathing exerciser according to claim 1, wherein the adjustable throttling device and the controlled throttling device, installed in the channels of communication of the second chamber with the atmosphere and with the third chamber, comprise a three-way mixing valve with two adjustable channels to reduce respiratory mixture resistance in one of the channels and at the same time to increase respiratory mixture resistance in the other channel, and vice versa, using a single control handle.

12. The breathing exerciser according to claim 1, wherein the adjustable throttling device and the controlled throttling device, installed in the channels of communication of the second chamber with the atmosphere and with the third chamber, are in communication with the channel of communication of the first chamber with the second chamber, and comprise a three-way mixing valve with three regulated channels to reduce respiratory mixture resistance in one of the regulated channels and at the same time to increase respiratory mixture resistance in a second one of the regulated channels, and vice versa, as well as to independently regulate respiratory mixture resistance in a third one of the regulated channels with a single control handle faucet.

13. The breathing exerciser according to claim 1, wherein the first chamber is provided with at least one partition, the partition including means for generating acoustic vibrations.

14. The breathing exerciser according to claim 1, wherein the means for connecting the exerciser to the user's respiratory airways comprises a tube with a mouthpiece, or a hermetic face mask, or a hermetic helmet, or an airtight suit.

15. A breathing exerciser comprising a first chamber connected with a means for connecting the exerciser to an exerciser user's airways, a second chamber in communication with the first chamber, a third chamber in communication with the second chamber, means for regulating a respiratory mixture composition and means for regulating inhalation resistance and exhalation resistance, wherein the third chamber is flexible, the second chamber is in communication with an atmosphere, the first chamber is in communication with the second chamber by two parallel channels, the means for regulating the respiratory mixture composition comprises an adjustable throttling device, installed in a channel of communication of the second chamber with the third chamber, and an adjustable throttling device installed in a channel of communication of the second chamber with the atmosphere, and the means for regulating the inhalation resistance and exhalation resistance comprises series-connected check valves and adjustable throttling devices installed in the two parallel channels to provide respiratory mixture passages in said channels in opposite directions.

16. The breathing exerciser according to claim 15, wherein the adjustable throttling devices installed in the channels of communication of the second chamber with the atmosphere and with the third chamber comprise a three-way mixing valve with two regulated channels to reduce a respiratory mixture resistance in a regulated channel and at the same time to increase a respiratory mixture resistance in the other regulated channel, and vice versa, using a single controlling handle.

17. The breathing exerciser according to claim 15, wherein the series-connected check valves and adjustable throttling devices installed in the parallel channels of communication of the first chamber with the second chamber comprise non-return check valves with means for regulating flow throttling degree in a forward direction.

18. The breathing exerciser according to claim 17, wherein the means for regulating the flow throttling degree in the forward direction comprises an adjustable stop limiting movement of a locking member towards an opening of an adjacent check valve.

19. The breathing exerciser according to claim 15, wherein the series-connected check valves and adjustable throttling devices installed in the parallel channels of communication of the first chamber with the second chamber comprise a transverse partition fastened in a cylindrical housing, inner cups, installed inside the cylindrical housing on both sides of the partition to be rotated around a longitudinal axis and to contact the partition by cup bottoms, diametrically opposite pairs of openings formed in the partition and the cup bottoms, check valves comprising petals to overlap one of the cup bottom openings of an inner side of each of the cups, cup bottom openings located opposite to said openings with the check valves comprising slots; a cup bottom opening with a check valve and a bottom slot of the other cup are configured to be located axially with one of holes in the partition.

20. The breathing exerciser according to claim 15, wherein the first and the second chambers are located in an annular hollow housing, a cavity of which is divided into the first and the second chambers, communicating with each other.

21. A breathing exerciser comprising means for connecting the exerciser to an exerciser user's airways, a first chamber connected with said means, a second chamber communicating with the first chamber, a third chamber communicating with the second chamber, means for regulating a respiratory mixture composition, inhalation resistance and exhalation resistance, wherein the third chamber is flexible, the exerciser includes a respiratory mixture source, the second chamber is divided into two cavities, a first cavity of which is in communication with the first chamber, the third chamber and an atmosphere, a second cavity of said two cavities is in communication with the third chamber, with the respiratory mixture source, and with the first chamber; and the means for regulating the respiratory mixture composition, inhalation resistance and exhalation resistance comprises series-connected check valves and adjustable throttling devices installed in a channel of communication of the first chamber with the first cavity of the second chamber to direct flow towards the first cavity of the second chamber, in a channel of communication of the first cavity of the second chamber with the atmosphere to direct flow towards the atmosphere, in a channel of communication of the third chamber with the first cavity of the second chamber to direct flow towards the third chamber, in a channel of communication of the third chamber with the second cavity of the second chamber to direct flow towards the second cavity, in a channel of communication of the second cavity of the second chamber with the first chamber to direct flow towards the first chamber, and in a channel of communication of the second cavity of the second chamber with the respiratory mixture source to direct flow towards the second cavity of the second chamber.

22. The breathing exerciser according to claim 21, wherein the second cavity of the second chamber is in communication with the atmosphere as the source of the respiratory mixture.

23. The breathing exerciser according to claim 21, wherein the respiratory mixture source comprises a respiratory mixture preparation chamber communicating with the atmosphere and including a cavity containing natural or synthetic essential oils and/or herbs and/or herbal extracts; and/or mineral substances, with or without heating means.

24. The breathing exerciser according to claim 23, wherein the respiratory mixture preparation chamber is configured to receive therein an exerciser user's body, or a user's body part.

25. The breathing exerciser according to claim 21, wherein the respiratory mixture source includes an adjustable throttle device and a breathing bag.

26. The breathing exerciser according to claim 21, wherein said first and second chambers are located in an annular hollow housing comprising a cavity which is divided into the first chamber, the first cavity of the second chamber and the second cavity of the second chamber, interconnected between each other.

27. The breathing exerciser according to claim 21, wherein the adjustable throttling devices installed in the channels of communication of the first cavity of the second chamber with the atmosphere and the third chamber and also the adjustable throttling devices installed in the channels of communication of the second cavity of the second chamber with the third chamber and with the respiratory mixture source comprise three-way mixing valves, each with two regulated channels to reduce respiratory mixture resistance in one of the regulated channels and at the same time to increase respiratory mixture resistance in the other regulated channel, and vice versa, using a single controlling handle.

28. The breathing exerciser according to claim 21, wherein the adjustable throttling devices installed in the channels of communication of the first cavity of the second chamber with the atmosphere, with the first chamber and with the third chamber, as well as the adjustable throttling devices installed in the channels of communication of the second cavity of the second chamber with the third chamber, with the respiratory mixture source and with the first chamber comprise three-way mixing valves, each with three adjustable channels to reduce respiratory mixture resistance in a first one of the three adjustable channels and at the same time to increase respiratory mixture resistance in a second one of the three adjustable channels, and vice versa, and to regulate independently respiratory mixture resistance in a third one of the three adjustable channels using a single handles of regulation.

29. The breathing exerciser according to claim 21, wherein the series-connected check valves and the adjustable throttling devices installed in the channel of communication of the first chamber with the first cavity of the second chamber, in the channel of communication of the first cavity of the second chamber with the atmosphere, in the channel of communication of the first cavity of the second chamber with the third chamber, in the channel of communication of the third chamber with the second cavity of the second chamber, in the channel of communication of the second cavity of the second chamber with the first chamber, and in the channel of communication of the second cavity of the second chamber with the respiratory mixture source, comprise check valves provided with a means for regulating flow throttling in a forward direction.

30. The breathing exerciser according to claim 21, wherein each of the adjustable throttling devices installed in the channels of communication of the first chamber with the first cavity and the second cavity of the second chamber, includes an outer cup and, installed inside said outer cup, an inner cup configured to be rotated around a longitudinal axis and wherein a bottom of the inner cup contacts a bottom of the outer cup; and openings in both cup bottoms are configured to overlap of each other and to form adjustable flow sections connecting the first chamber with the first and second cavities of the second chamber when the inner cup is turning independently; each of the adjustable throttling devices installed in the channels of communication of the first cavity of the second chamber with the atmosphere and with the third chamber and in the channels of communication of the second cavity of the second chamber with the third chamber and with the respiratory mixture source, comprises inner and outer cups with bottom openings and wall openings which are configured to overlap other mutually and, when independently turning the inner cups, to form adjustable flow sections connecting the first cavity of the second chamber with the atmosphere and with the third chamber and connecting the second cavity of the second chamber with the third chamber and with the respiratory mixture source, said openings configured to change values of flow cross bottom sections and flow cross wall sections of the cups when rotating each inner cups in opposite directions.

31. The breathing exerciser according to claim 21 wherein a respirator mixture pressure sensor and/or a respirator mixture composition sensor and/or a respirator mixture flow sensor is installed at least in one of the chambers or channels, and said sensors are adapted to provide visual representation of sensor readings to the user.

32. The breathing exerciser according to claim 31, wherein it is equipped with a computer system to control an operating mode, the computer system consisting of respiratory mixture pressure sensors and/or respiratory mixture composition sensors and/or respiratory mixture flow sensors installed at least in one channel or chamber of the exerciser, a processor with preset operating mode algorithms of the exerciser, and a monitor for the visual presentation of readings to the user about the operating mode of the exerciser.

* * * * *